(12) United States Patent
Roe

(10) Patent No.: US 8,998,870 B2
(45) Date of Patent: Apr. 7, 2015

(54) REUSABLE WEARABLE ABSORBENT ARTICLES WITH ANCHORING SYSTEMS

(75) Inventor: Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 894 days.

(21) Appl. No.: 12/687,437

(22) Filed: Jan. 14, 2010

(65) Prior Publication Data

US 2010/0179498 A1    Jul. 15, 2010

Related U.S. Application Data

(60) Provisional application No. 61/144,883, filed on Jan. 15, 2009.

(51) Int. Cl.
| | |
|---|---|
| *A61F 13/15* | (2006.01) |
| *A61F 13/56* | (2006.01) |
| *A61F 13/49* | (2006.01) |
| *A61F 13/505* | (2006.01) |
| *A61F 13/66* | (2006.01) |

(52) U.S. Cl.
CPC ............. *A61F 13/5622* (2013.01); *A61F 13/66* (2013.01); *A61F 13/49003* (2013.01); *A61F 13/49014* (2013.01); *A61F 13/505* (2013.01)

(58) Field of Classification Search
CPC .................. A61F 13/49003; A61F 13/49004; A61F 13/49006; A61F 13/66; A61F 13/74; A61F 13/76
USPC ............... 604/393, 397, 396, 398, 385.15, 604/385.24, 385.25, 385.29
See application file for complete search history.

(56) References Cited

U.S. PATENT DOCUMENTS

| | | | |
|---|---|---|---|
| 2,119,610 A | 6/1938 | Robert | |
| 2,530,647 A | 11/1950 | Buchler | |
| 2,688,328 A | 9/1954 | Marcus | |
| 2,793,642 A * | 5/1957 | Andruhovici | ................ 604/397 |
| 3,077,193 A | 2/1963 | Mann | |
| 3,496,259 A | 2/1970 | Guenther | |
| 3,560,292 A | 2/1971 | Butter | |
| 3,719,736 A | 3/1973 | Woodruff | |
| 3,735,424 A | 5/1973 | Maggio et al. | |
| 3,860,003 A | 1/1975 | Buell | |
| 3,911,173 A | 10/1975 | Sprague, Jr. | |
| 3,926,189 A | 12/1975 | Taylor | |
| 3,929,135 A | 12/1975 | Thompson | |

(Continued)

FOREIGN PATENT DOCUMENTS

| | | |
|---|---|---|
| AU | 642 386 B3 | 10/1993 |
| CA | 2 103 537 | 2/1995 |

(Continued)

OTHER PUBLICATIONS

International Search Report and Written Opinion, PCT/US2010/021168, mailed Jun. 14, 2010, 12 pages.

(Continued)

*Primary Examiner* — Lynne Anderson
*Assistant Examiner* — Bradley Philips
(74) *Attorney, Agent, or Firm* — Christian M. Best; Charles R. Ware

(57) ABSTRACT

Reusable wearable absorbent articles with anchoring systems.

12 Claims, 6 Drawing Sheets

(56) References Cited

U.S. PATENT DOCUMENTS

| | | | |
|---|---|---|---|
| 3,955,575 A | 5/1976 | Okuda | |
| 4,022,210 A | 5/1977 | Glassman | |
| 4,072,150 A | 2/1978 | Glassman | |
| 4,081,301 A | 3/1978 | Buell | |
| 4,116,892 A | 9/1978 | Schwarz | |
| 4,195,634 A | 4/1980 | DiSalvo et al. | |
| 4,223,059 A | 9/1980 | Schwarz | |
| 4,265,245 A | 5/1981 | Glassman | |
| 4,284,454 A | 8/1981 | Joa | |
| 4,324,246 A | 4/1982 | Mullane et al. | |
| 4,326,302 A | 4/1982 | Lowe et al. | |
| 4,338,939 A | 7/1982 | Daville | |
| 4,342,314 A | 8/1982 | Radel et al. | |
| 4,352,356 A | 10/1982 | Tong | |
| 4,438,167 A | 3/1984 | Schwarz | |
| 4,463,045 A | 7/1984 | Ahr et al. | |
| 4,475,912 A | 10/1984 | Coates | |
| 4,496,360 A | 1/1985 | Joffe et al. | |
| 4,573,986 A | 3/1986 | Minetola et al. | |
| 4,578,073 A | 3/1986 | Dysart et al. | |
| 4,579,556 A | 4/1986 | Mcfarland | |
| 4,582,550 A | 4/1986 | Sigl | |
| 4,597,760 A | 7/1986 | Buell | |
| 4,597,761 A | 7/1986 | Buell | |
| 4,609,518 A | 9/1986 | Curro et al. | |
| 4,610,678 A | 9/1986 | Weisman et al. | |
| 4,615,695 A | 10/1986 | Cooper | |
| 4,625,245 A | 11/1986 | White | |
| 4,629,643 A | 12/1986 | Curro et al. | |
| 4,643,726 A | 2/1987 | Gegelys | |
| 4,650,483 A | 3/1987 | Joffe | |
| 4,657,539 A | 4/1987 | Hasse | |
| 4,661,102 A | 4/1987 | Shikata et al. | |
| 4,673,402 A | 6/1987 | Weisman et al. | |
| 4,695,278 A | 9/1987 | Lawson | |
| 4,701,170 A | 10/1987 | Wilson et al. | |
| 4,704,114 A | 11/1987 | Wilson et al. | |
| 4,704,116 A | 11/1987 | Enloe | |
| 4,710,187 A | 12/1987 | Boland et al. | |
| 4,747,846 A | 5/1988 | Boland et al. | |
| 4,756,709 A | 7/1988 | Stevens | |
| 4,770,656 A | 9/1988 | Proxmire et al. | |
| 4,785,996 A | 11/1988 | Ziecker et al. | |
| 4,795,452 A | 1/1989 | Blaney et al. | |
| 4,795,454 A | 1/1989 | Dragoo | |
| 4,808,176 A | 2/1989 | Kielpikowski | |
| 4,808,177 A | 2/1989 | Desmarais et al. | |
| 4,808,178 A | 2/1989 | Aziz et al. | |
| 4,816,026 A | 3/1989 | Richardson | |
| 4,834,735 A | 5/1989 | Alemany et al. | |
| 4,834,736 A | 5/1989 | Boland et al. | |
| 4,834,737 A | 5/1989 | Khan | |
| 4,834,738 A | 5/1989 | Kielpikowski et al. | |
| 4,842,666 A | 6/1989 | Werenicz | |
| 4,872,871 A | 10/1989 | Proxmire et al. | |
| 4,888,231 A | 12/1989 | Angstadt | |
| 4,892,536 A | 1/1990 | Desmarais et al. | |
| 4,892,598 A | 1/1990 | Stevens et al. | |
| 4,906,243 A | 3/1990 | Dravland | |
| 4,908,247 A | 3/1990 | Baird et al. | |
| 4,909,803 A | 3/1990 | Aziz et al. | |
| 4,955,880 A | 9/1990 | Rodriquez | |
| 4,961,736 A | 10/1990 | McCloud | |
| 4,964,857 A | 10/1990 | Osborn | |
| 4,968,311 A | 11/1990 | Chickering et al. | |
| 4,968,312 A | 11/1990 | Khan | |
| 4,978,046 A | 12/1990 | Hagmann et al. | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,019,068 A | 5/1991 | Perez et al. | |
| 5,021,051 A | 6/1991 | Hiuke | |
| 5,032,120 A | 7/1991 | Freeland et al. | |
| 5,037,416 A | 8/1991 | Allen et al. | |
| 5,069,672 A | 12/1991 | Wippler et al. | |
| 5,087,253 A | 2/1992 | Cooper | |
| 5,108,385 A | 4/1992 | Snyder | |
| 5,127,108 A | 7/1992 | Weiss | |
| 5,137,537 A | 8/1992 | Herron et al. | |
| 5,141,870 A | 8/1992 | Bedbrook et al. | |
| 5,147,345 A | 9/1992 | Young et al. | |
| 5,156,793 A | 10/1992 | Buell et al. | |
| 5,167,897 A | 12/1992 | Weber et al. | |
| 5,185,011 A | 2/1993 | Strasser | |
| 5,202,173 A | 4/1993 | Wu et al. | |
| 5,207,663 A | 5/1993 | McQueen | |
| 5,210,882 A | 5/1993 | Moretz et al. | |
| 5,217,447 A | 6/1993 | Gagnon | |
| 5,234,423 A | 8/1993 | Alemany et al. | |
| 5,254,111 A | 10/1993 | Cancio et al. | |
| 5,260,345 A | 11/1993 | Desmarais et al. | |
| 5,261,901 A | 11/1993 | Guay | |
| 5,269,775 A | 12/1993 | Freeland et al. | |
| 5,283,910 A | 2/1994 | Flint | |
| 5,296,184 A | 3/1994 | Wu et al. | |
| 5,306,267 A | 4/1994 | Hahn et al. | |
| 5,342,338 A | 8/1994 | Roe | |
| 5,354,597 A | 10/1994 | Capik et al. | |
| 5,360,422 A | 11/1994 | Brownlee et al. | |
| 5,368,584 A | 11/1994 | Clear et al. | |
| 5,368,585 A | 11/1994 | Dokken | |
| 5,387,207 A | 2/1995 | Dyer et al. | |
| 5,401,266 A | 3/1995 | Runeman et al. | |
| 5,405,342 A | 4/1995 | Roessler et al. | |
| 5,415,650 A | 5/1995 | Sigl | |
| 5,435,014 A * | 7/1995 | Moretz et al. | 2/403 |
| 5,458,591 A | 10/1995 | Roessler et al. | |
| 5,476,457 A | 12/1995 | Roessler et al. | |
| 5,509,915 A | 4/1996 | Hanson et al. | |
| 5,514,121 A | 5/1996 | Roe et al. | |
| 5,518,801 A | 5/1996 | Chappell et al. | |
| 5,554,142 A | 9/1996 | Dreier et al. | |
| 5,562,648 A * | 10/1996 | Peterson | 604/370 |
| 5,571,096 A | 11/1996 | Dobrin et al. | |
| 5,607,760 A | 3/1997 | Roe | |
| 5,609,587 A | 3/1997 | Roe | |
| 5,613,959 A | 3/1997 | Roessler et al. | |
| 5,624,425 A | 4/1997 | Gray et al. | |
| 5,625,222 A | 4/1997 | Yoneda et al. | |
| 5,635,191 A | 6/1997 | Roe et al. | |
| H1670 H | 7/1997 | Aziz et al. | |
| 5,643,191 A | 7/1997 | Buckberg et al. | |
| 5,643,588 A | 7/1997 | Roe et al. | |
| 5,667,503 A | 9/1997 | Roe et al. | |
| 5,671,615 A | 9/1997 | Kjærgaard et al. | |
| 5,716,349 A | 2/1998 | Taylor et al. | |
| H1732 H | 6/1998 | Johnson | |
| 5,769,838 A | 6/1998 | Buell et al. | |
| 5,772,649 A | 6/1998 | Siudzinski | |
| 5,776,121 A | 7/1998 | Roe et al. | |
| 5,795,347 A | 8/1998 | Roe et al. | |
| 5,795,348 A | 8/1998 | Roe et al. | |
| 5,795,384 A | 8/1998 | Coyle et al. | |
| 5,814,037 A | 9/1998 | Coates | |
| 5,827,261 A | 10/1998 | Osborn et al. | |
| 5,843,065 A | 12/1998 | Wyant | |
| 5,843,267 A | 12/1998 | Cashaw et al. | |
| H1788 H | 2/1999 | Christon et al. | |
| 5,865,823 A | 2/1999 | Curro | |
| 5,906,603 A | 5/1999 | Roe et al. | |
| 5,911,713 A | 6/1999 | Yamada et al. | |
| 5,938,648 A | 8/1999 | Lavon et al. | |
| 5,941,864 A | 8/1999 | Roe | |
| 5,947,946 A | 9/1999 | Fisher et al. | |
| 5,968,025 A | 10/1999 | Roe et al. | |
| 5,984,911 A | 11/1999 | Siebers et al. | |
| 6,007,528 A | 12/1999 | Osborn | |
| 6,010,491 A | 1/2000 | Roe et al. | |
| 6,120,487 A | 9/2000 | Ashton | |
| 6,142,983 A | 11/2000 | Surprise et al. | |
| 6,207,738 B1 | 3/2001 | Zuckerman et al. | |
| 6,229,061 B1 | 5/2001 | Dragoo et al. | |
| 6,240,569 B1 | 6/2001 | Van Gompel et al. | |

(56) References Cited

U.S. PATENT DOCUMENTS

| | | |
|---|---|---|
| 6,251,097 B1 | 6/2001 | Kline et al. |
| 6,254,583 B1 | 7/2001 | Coates |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 * | 7/2002 | Gustafsson .............. 604/385.01 |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,526,631 B1 | 3/2003 | Alberg et al. |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 | 6/2003 | Ono et al. |
| 6,579,273 B2 | 6/2003 | Dupuy |
| 6,623,466 B1 | 9/2003 | Richardson |
| 6,669,618 B2 | 12/2003 | Reising et al. |
| 6,680,422 B2 | 1/2004 | Roe |
| 6,709,423 B1 | 3/2004 | Herrlein et al. |
| 6,716,441 B1 | 4/2004 | Osborne et al. |
| 6,764,477 B1 | 7/2004 | Chen et al. |
| 6,764,478 B2 | 7/2004 | Ashton et al. |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,921,393 B2 | 7/2005 | Tears et al. |
| 6,936,039 B2 | 8/2005 | Kline et al. |
| 6,964,720 B2 | 11/2005 | Schneider et al. |
| 6,966,720 B2 | 11/2005 | Moss |
| 6,980,872 B2 | 12/2005 | Kano et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,166,095 B1 | 1/2007 | Coates |
| 7,211,531 B2 | 5/2007 | Schneider et al. |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,344,526 B2 * | 3/2008 | Yang et al. .............. 604/393 |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Frank et al. |
| 7,537,587 B2 | 5/2009 | Carstens |
| 7,576,019 B2 | 8/2009 | Bond et al. |
| 7,591,811 B2 | 9/2009 | Wilkinson |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,770 B2 | 8/2010 | Wang et al. |
| 7,776,771 B2 | 8/2010 | Autran et al. |
| 7,820,875 B2 | 10/2010 | Roe et al. |
| 7,824,387 B2 | 11/2010 | LaVon |
| 7,833,211 B2 | 11/2010 | Mansfield |
| 7,842,627 B2 | 11/2010 | Gao et al. |
| 7,872,169 B2 | 1/2011 | Ruiz et al. |
| 7,875,014 B2 | 1/2011 | Hendren et al. |
| 7,887,527 B2 | 2/2011 | Hayashi et al. |
| 7,914,507 B1 | 3/2011 | Magee |
| 7,993,322 B2 * | 8/2011 | Brud et al. .............. 604/396 |
| 8,118,801 B2 | 2/2012 | Macura et al. |
| 8,158,043 B2 | 4/2012 | Gibson et al. |
| 8,262,635 B2 | 9/2012 | Labit et al. |
| 2002/0010452 A1 | 1/2002 | Dupuy |
| 2002/0035747 A1 | 3/2002 | Kusibojoska et al. |
| 2002/0128619 A1 | 9/2002 | Carlbark et al. |
| 2003/0088220 A1 | 5/2003 | Molander et al. |
| 2003/0091807 A1 | 5/2003 | Desai et al. |
| 2003/0114805 A1 | 6/2003 | Rainville et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0127867 A1 | 7/2004 | Odorzynski et al. |
| 2005/0033258 A1 | 2/2005 | Suzuki et al. |
| 2005/0096624 A1 * | 5/2005 | Hoshino et al. .......... 604/385.27 |
| 2005/0148974 A1 * | 7/2005 | Datta et al. .............. 604/385.01 |
| 2005/0164587 A1 | 7/2005 | Melik et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 * | 3/2006 | Ashton et al. .............. 604/396 |
| 2006/0058766 A1 | 3/2006 | Mueller et al. |
| 2006/0069372 A1 | 3/2006 | Chakravarty et al. |
| 2006/0087053 A1 | 4/2006 | O'Donnell et al. |
| 2006/0095012 A1 | 5/2006 | Cohen |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | LaVon |
| 2006/0247599 A1 * | 11/2006 | Mullen et al. .............. 604/393 |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 * | 11/2006 | Carstens .............. 604/396 |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0123834 A1 | 5/2007 | McDowall et al. |
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1 | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdonl et al. |
| 2008/0004586 A1 | 1/2008 | Lodge et al. |

(56) References Cited

U.S. PATENT DOCUMENTS

| | | |
|---|---|---|
| 2008/0004587 A1 | 1/2008 | Lodge et al. |
| 2008/0004589 A1 | 1/2008 | Roe et al. |
| 2008/0004590 A1* | 1/2008 | Lodge et al. .......... 604/396 |
| 2008/0004591 A1 | 1/2008 | Desai et al. |
| 2008/0004592 A1 | 1/2008 | Lodge et al. |
| 2008/0004593 A1* | 1/2008 | Lodge et al. .......... 604/401 |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0081854 A1 | 4/2008 | Wang et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1* | 5/2008 | Lodge et al. .......... 604/385.03 |
| 2008/0188822 A1* | 8/2008 | Lodge et al. .......... 604/385.03 |
| 2008/0215028 A1 | 9/2008 | Brown et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0127742 A1 | 5/2009 | Qureshi et al. |
| 2009/0216209 A1 | 8/2009 | Ekstrom |
| 2010/0004616 A1 | 1/2010 | Nakamura |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2010/0331803 A1 | 12/2010 | Saito |
| 2011/0137277 A1 | 6/2011 | Hough et al. |
| 2012/0049404 A1 | 3/2012 | Gibson et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 | 11/1996 |
| CA | 2 365 577 | 6/2003 |
| DE | 103 03 903 | 11/2003 |
| EP | 0 023 804 | 2/1981 |
| EP | 0 187 726 | 7/1986 |
| EP | 319314 | 6/1989 |
| EP | 0667136 | 8/1995 |
| EP | 549988 | 6/1998 |
| EP | 796069 | 8/2000 |
| EP | 763353 | 6/2002 |
| FR | 2532337 | 3/1984 |
| GB | 112638 | 1/1918 |
| GB | 2 440 314 | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 U | 11/1990 |
| JP | 06-178795 | 1/1993 |
| JP | 2001-346826 | 12/2001 |
| JP | 2002-325786 | 11/2002 |
| JP | 2003-038564 | 2/2003 |
| JP | 2003-093438 | 4/2003 |
| JP | 2003-190213 A | 7/2003 |
| JP | 2004-261332 | 9/2004 |
| JP | 2005-6827 A | 1/2005 |
| JP | 2005-111119 A | 4/2005 |
| JP | 2005-118533 | 5/2005 |
| JP | 3109189 | 5/2005 |
| JP | 2007-244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 | 11/1991 |
| WO | WO-92/01431 | 2/1992 |
| WO | WO-92/15444 | 9/1992 |
| WO | WO-94/15563 | 7/1994 |
| WO | WO-94/15663 | 7/1994 |
| WO | WO-95/10992 | 4/1995 |
| WO | WO-95/16746 | 6/1995 |
| WO | WO-96/17572 | 6/1996 |
| WO | WO 96/24319 A1 | 8/1996 |
| WO | WO-96/32912 | 10/1996 |
| WO | WO-00/65348 | 11/2000 |
| WO | WO-02/066086 | 8/2002 |
| WO | WO-2004/060229 | 7/2004 |
| WO | WO 2005/039469 A1 | 5/2005 |
| WO | WO-2005/052052 | 6/2005 |
| WO | WO 2005/096855 A1 | 10/2005 |
| WO | WO-2005/097031 | 10/2005 |
| WO | WO-2008/030984 | 3/2008 |
| WO | WO-2008/120959 | 10/2008 |
| WO | WO 2008/142634 A2 | 11/2008 |
| WO | WO-2010/053006 | 5/2010 |
| WO | WO 2010078661 | 7/2010 |

OTHER PUBLICATIONS

All Office Actions, U.S. Appl. No. 12/687,444.
All Office Actions, U.S. Appl. No. 12/691,929.
All Office Actions, U.S. Appl. No. 12/687,554.
US 5,583,910, 12/1996, Flint (withdrawn).
www.gdiapers.com—Web pages dated Nov. 23, 2009.
www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).

(56) References Cited

OTHER PUBLICATIONS

"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), the Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
Data Sheet, p. V-17, from "Baby Diaper Design Update—1987", publication of Marketing Technology Service, Inc., product believed to be a product of Kao Corp. sold in Japan in 1986 or 1987.
All Office Actions, U.S. Appl. No. 13/183,952.
All Office Actions, U.S. Appl. No. 12/687,493.
All Office Actions, U.S. Appl. No. 12/687,507.
All Office Actions, U.S. Appl. No. 12/687,527.
All Office Actions, U.S. Appl. No. 12/687,538.
All Office Actions, U.S. Appl. No. 12/785,152.
All Office Actions, U.S. Appl. No. 12/785,166.
All Office Actions, U.S. Appl. No. 12/785,181.
ISR and Written Opinion PCT/US2010/021168, date of mailing Jun. 14, 2010.
All Office Actions, Responses and Claims, U.S. Appl. No. 13/183,952.
All Office Actions, Responses and Claims, U.S. Appl. No. 12/687,493.
All Office Actions, Responses and Claims, U.S. Appl. No. 12/687,507.
All Office Actions, Responses and Claims, U.S. Appl. No. 12/687,527.
All Office Actions, Responses and Claims, U.S. Appl. No. 12/687,538.
All Office Actions, Responses and Claims, U.S. Appl. No. 12/687,554.
All Office Actions, Responses and Claims, U.S. Appl. No. 12/687,444.
All Office Actions, Responses and Claims, U.S. Appl. No. 12/785,152.
All Office Actions, Responses and Claims, U.S. Appl. No. 12/785,166.
All Office Actions, Responses and Claims, U.S. Appl. No. 12/785,181.
All Office Actions, Responses and Claims, U.S. Appl. No. 14/053,014.
All Office Actions, Responses and Claims, U.S. Appl. No. 12/841,553.
All Office Actions, Responses and Claims, U.S. Appl. No. 12/841,467.
All Office Actions, Responses and Claims, U.S. Appl. No. 13/859,015.
All Office Actions, Responses and Claims, U.S. Appl. No. 12/841,600.
All Office Actions, Responses and Claims, U.S. Appl. No. 14/014,440.

\* cited by examiner

US 8,998,870 B2

REUSABLE WEARABLE ABSORBENT ARTICLES WITH ANCHORING SYSTEMS

CROSS REFERENCE TO RELATED APPLICATIONS

This application claims the benefit of U.S. provisional patent application 61/144,883 filed Jan. 15, 2009, the substance of which is hereby incorporated by reference.

FIELD

In general, embodiments of the present disclosure relate to wearable absorbent articles. In particular, embodiments of the present disclosure relate to reusable wearable absorbent articles with anchoring systems.

BACKGROUND

Wearable absorbent articles include reusable diapers and reusable incontinence undergarments. A wearable absorbent article can receive and contain bodily waste while being worn by a wearer. Such articles can be made with various materials in a number of configurations. The design of a wearable absorbent article can affect the way that the article fits on a wearer. Unfortunately, some wearable absorbent articles fit wearers poorly. As an example, some wearable absorbent articles can sag or slip down on a wearer. A wearable absorbent article that sags or slips down on a wearer can feel uncomfortable, look unattractive, and perform poorly as the article tends to leak.

DETAILED DESCRIPTION

Figure 1A:
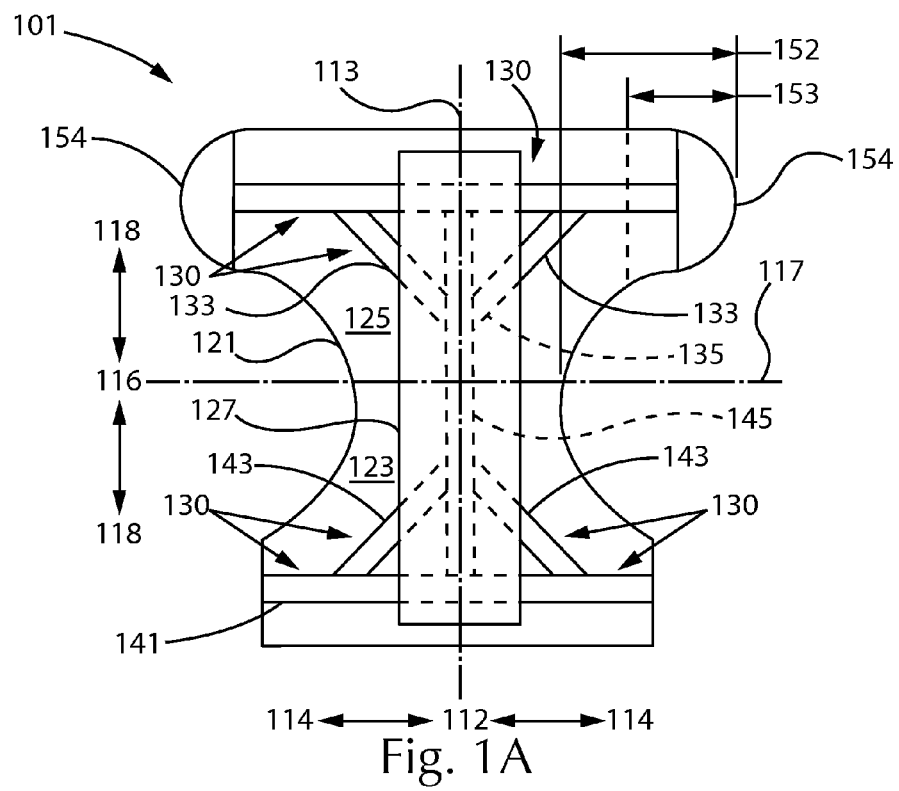
FIG. 1A illustrates a plan view of an inside of a front fastenable wearable absorbent article, which includes a first anchoring system.

Embodiments of the present disclosure include wearable absorbent articles with anchoring systems that fit wearers well. The wearable absorbent articles can be configured as reusable wearable absorbent articles or as disposable wearable absorbent articles. The designs of these articles help prevent the articles from sagging or slipping down on a wearer. As a result, the wearable absorbent articles of the present disclosure can feel comfortable, look attractive, and perform well as the articles tend to stay in place on wearers and not leak.

Absorbent articles include products for sanitary protection, for hygienic use, and the like. Some absorbent articles are wearable. A wearable absorbent article is configured to be worn on or around a lower torso of a body of a wearer. Examples of wearable absorbent articles include diapers, training pants, and incontinence undergarments.

A wearable absorbent article can include an absorbent core. Throughout the present disclosure, the term absorbent core refers to a part of a wearable absorbent article configured to absorb bodily exudates received into the article from a body of a wearer. An absorbent core can be configured in various ways, as will be understood by one of ordinary skill in the art. An absorbent core can include one or more absorbent materials, such as wood pulp and/or superabsorbent particles, and may include one or more additional compositions, materials, or structures for receiving, containing, storing, and/or treating bodily waste, as known in the art. Further, an absorbent core may include one or more of compositions such as lotions, perfumes, and sensates, on an outer surface and/or within the assembly. An absorbent core can be configured as a bucket-shaped absorbent core, a removable absorbent core, a replaceable absorbent core, etc. An absorbent core can be part of an absorbent core assembly, comprising one or more layers such as a liquid-permeable topsheet, an acquisition layer, a distribution layer, a storage layer, and a liquid impermeable backsheet. An absorbent core assembly may also include one or more of various structures, such as barrier leg cuffs, a feces containment compartment, a wetness indicator, fasteners for retaining the core within an article, disposal tapes, etc.

In various embodiments, an absorbent core can be configured as described in U.S. application Ser. Nos. 12/141,122; 12/141,124; 12/141,126; 12/141,128; 12/141,130; 12/141,132; 12/141,134; 12/141,141; 12/141,143; and 12/141,146, each of which is hereby incorporated by reference. These applications generally describe absorbent core constructions that minimize or eliminate the need for and inclusion of airfelt or other forms of cellulose fiber in combination with super absorbent particles.

A wearable absorbent article can also include an outer cover. Throughout the present disclosure, the term outer cover refers to a part of a wearable absorbent article forming an outer surface of the article (sometimes referred to as a backsheet), extending beyond the edges of the absorbent core, usually covering a significant portion of the buttocks of the wearer, and generally shaped to resemble the appearance of an undergarment. An outer cover can be configured in various ways, as described herein. In various embodiments, an outer cover can coincide with and/or define a chassis of a wearable absorbent article.

Some absorbent articles are disposable. A disposable absorbent article is configured to be disposed of after a single use (e.g., not intended to be reused, restored, or laundered). Examples of disposable absorbent articles include disposable diapers, disposable training pants, disposable incontinence undergarments, as well as feminine care pads and liners.

Some absorbent articles are reusable. The term reusable, as used herein, means that a referenced material, component, or all of an absorbent article is configured to be restored and/or reused for more than one usage cycle (e.g. a diaper change). In some reusable absorbent articles, part, or parts, or substantially all, or all of the articles may be launderable or laundering resistant, as defined and described herein. As an example, a wearable absorbent article can include an outer cover that is launderable or laundering resistant. In other reusable absorbent articles, part, or parts, or substantially all, or all of the articles may not be launderable or may not be laundering resistant. For example, an absorbent article can be configured as a reusable absorbent article by using materials, such as nonwovens, that are used in disposable articles, such as diapers.

In various embodiments, a reusable outer cover can be configured to perform various functions, which provide various benefits to a wearer of the article and/or to a care giver for the wearer. In various embodiments, a reusable outer cover can be configured to provide liquid impermeability, which can help the absorbent article contain bodily waste. In various embodiments, a reusable outer cover can be configured to provide vapor permeability (e.g. breathability), which can help the wearer maintain healthy skin. In various embodiments, a reusable outer cover can be configured to be elastically extensible, inelastically extensible, and/or inextensible, in one or more particular directions. In various embodiments, at least a portion of a reusable outer cover, such as a portion of an inner layer, may be absorbent to control minor leakage events from the absorbent core.

Specifically, part, or parts, or substantially all, or all of a reusable outer cover thereof can be configured to extend and relax to particular degrees, while the article is being applied to a wearer, while the article is being worn by a wearer, and while the article is containing bodily waste. A reusable outer cover can be configured to extend easily while the article is being applied to a wearer, to help facilitate application. A reusable outer cover can also be configured to extend adequately while the article is being worn, to help accommodate the wearer's movement while provide a conforming fit. A reusable outer cover can further be configured to relax (i.e. contract), properly with sufficient tension to provide sustained fit while the article is being worn, and to help support the absorbent core. It is contemplated that any reusable outer cover disclosed herein can be used with any embodiment of a wearable absorbent article disclosed herein.

The term launderable, as used herein, means that a referenced material, component, or all of an absorbent article is configured to withstand a large number (e.g. at least 10, in some embodiments up to 50, in other embodiments more than 50) of cycles of machine washing and machine drying (as defined by AATCC Test Method 124-2001 as described herein), without significant degradation to the appearance or performance of the article that would render it unsuitable for its intended functionality and/or use. As used herein, the term "wash" or "wash cycle" refers to a cycle of machine washing and machine drying, as described above. Since hand-washing and line-drying are typically much less stressful on an absorbent article than machine washing and machine drying, it is expected that a material, component, or article that is machine washable and machine dryable, should also be hand-washable and hand-dryable for at least as many cycles. As an example, a reusable wearable absorbent article can include an outer cover that is launderable. Launderable articles are designed to be suitable for use after many washings, similar to types of clothing.

The term laundering resistant, as used herein, means that a referenced material, or component, or all of an absorbent article is configured to withstand a small number (e.g. at least one, in some embodiments up to 5, in other embodiments more than 5) of cycles of machine washing and drying (as defined by AATCC Test Method 124-2001 and as described herein), without significant degradation to the appearance or performance of the article that would render it unsuitable for its intended functionality and/or use. As an example, a reusable wearable absorbent article can include an outer cover that is laundering resistant. Laundering resistant articles generally experience degradation after fewer laundering cycles than launderable articles. For example, a laundering resistant material may experience significant degradation in appearance or performance after 5 or 10 wash cycles.

Exemplary Launderable Outer Cover

Following is a description of an exemplary launderable outer cover for use in a front fastenable wearable absorbent article. The exemplary launderable outer cover includes an outer layer, an inner layer, left and right side leg bands, front and back waist bands, an anchoring band, a landing zone, side ear fasteners, side ear stiffeners, and absorbent core fastening elements.

Throughout the present disclosure, the term right side refers to a side of a material that will be on the outside of the completed article, and the term wrong side refers to a side of a material that will be on the inside of the completed article (or, in embodiments having multiple layers, between layers of the completed article). When complete, the right side of the outer layer will be the garment-facing side and the right side of the inner layer will be the wearer-facing side.

Each element of the exemplary launderable outer cover is formed from one or more particular materials. The outer layer material is a soft and stretchable knit fabric made of Modal with Lycra. For example, the outer layer material can be 95% Modal and 5% Lycra. The inner layer material is made from two materials. The inner layer material that is configured to be disposed in a back of the article is configured to be laterally stretchable, to provide a comfortable fit. The back inner layer material is a soft and stretchable knit fabric made of polyester with Spandex. For example, the inner layer material can be 94% polyester and 6% Spandex. The inner layer material that is configured to be disposed in a crotch and front of the article is configured to be hydrophobic, to resist urine penetration. For example, the inner layer material can be 90% Nylon Tricot and 10% Spandex.

The leg and waist bands are formed from inner material, which is elastic, and an outer material, which is a soft, extensible fabric. For example, the inner elastic band material can be natural elastic, about 10 mm wide. The inner elastic band material is similar to the back inner layer material. The outer fabric band material is similar to the outer layer material.

The anchoring band material is a strip of stretchable knit fabric made of polyester with Spandex. For example, the stretchable knit fabric can be 90% polyester and 10% Spandex, 25 mm wide. The anchoring band material is configured to have a higher modulus of elasticity and a lower elastic Hysteresis than the outer layer material. The landing zone and the side ear fasteners comprise a mechanical hook and loop fastening system with sewable patches of loops and hooks, respectively. The ear stiffener material is a woven fusible interfacing, to help the ears resist folding or buckling. The absorbent core fastening elements are also patches of loops configured to fasten with hooks on an absorbent core.

To make the exemplary launderable outer cover, first, each material is cut to a desired shape. The outer layer material and the inner layer material are cut to the same shape, which is the overall shape of the outer cover.

For the leg bands, two pieces of the inner elastic band material are cut; each to a length for contractible leg cuff portions of the left or right longitudinal side of the outer cover. For example the length of the inner elastic leg band can be about 220 mm. Also, two pieces of the outer fabric band material are cut; each to a particular length and a width such that each piece of the outer fabric leg band material can be folded in half lengthwise to envelope a piece of the inner elastic leg band material.

Similarly, for the waist bands, two pieces of the inner elastic band material are cut; each to a length for contractible waist edge portions of the front or back end of the outer cover. For example the length of the inner elastic waist band can be about 245 mm. Further, two pieces of the outer fabric band material are cut; each to a particular length and a width so that each piece of the outer fabric waist band material can folded in half lengthwise to envelope a piece of the inner elastic waist band material.

One anchoring band is cut to length to fit from one back side ear to the other back side ear. Two side ear fasteners are cut to fit on the side ears on the back of the outer cover. One landing zone is cut to accommodate the side ear fasteners and to fit on the front of the outer cover. Eight side ear stiffeners are cut to fit inside the side ears on each side in the front and back of the outer cover. Two absorbent core fastener elements are cut to accommodate hooks on an absorbent core.

Second, the cut materials are assembled together. The landing zone is sewn to the right side of front of the outer cover. Four of the side ear stiffeners are fused to wrong side of the outer layer, one each at the left and right side ears on the front and back.

The leg bands are sewn to the wrong side of the inner layer and to the wrong side of the outer layer at the contractible leg cuff portions on the left and right longitudinal sides of the outer cover. During this sewing, a central portion of the each leg band is prestretched while the inner layer and the outer layer are substantially relaxed. For each leg band, the ends of the inner elastic leg band material are secured, but a central portion is free to move inside of the outer fabric leg band material.

Similarly, the waist bands are sewn to the wrong side of the inner layer and to the wrong side of the outer layer at the contractible waist edge portions on the front and back ends of the outer cover. During this sewing, a central portion of the each leg band is prestretched while the inner layer and the outer layer are substantially relaxed. For each waist band, the ends of the inner elastic waist band material are secured, but a central portion is free to move inside of the outer fabric waist band material.

The anchoring band is sewn to the wrong side of the inner layer, at the back side ear and the front side ear. During this sewing, both the anchoring band and the inner layer are substantially relaxed; that is, when they are laid down flat together, neither element is prestretched with respect to the other. A central portion of the anchoring band is not sewn to the inner layer. The side ear fasteners are sewn to the right side of the inner layer, at the left back side ear and the right back side ear. The absorbent core fastening elements are sewn to the right side of front and back of the inner layer. Four of the side ear stiffeners are fused to wrong side of the inner layer, one each at the left and right side ears on the front and back. The inner layer and the outer layer are then sewn together and inverted in order to be right side out. The exemplary launderable outer cover is complete. In the completed outer cover, the central portion of the anchoring band is free to move with respect to the inner layer and the outer layer. Also, in the completed outer cover, the anchoring band is not prestretched with respect to the inner layer or the outer layer.

This exemplary launderable outer cover is intended as a non-limiting example, and can be varied in numerous ways as described below. Any of the elements of the outer cover may comprise one or more subcomponents; that is, an element may be formed of more than one piece or type of material. Either or both layers of the outer cover may comprise a single layer of material or may comprise two or more layers and/or two or more materials. The inner layer may be stretchable in both the lateral and longitudinal directions. The inner layer may be treated to make it more hydrophobic. The inner layer may have varying stretchability, hydrophobicity, and/or breathability across its area.

The outer cover may also have varying stretchability, hydrophobicity, and/or breathability across its area. The outer cover may have no anchoring band or may have any number of anchoring bands or other anchoring system components. As an example, a launderable outer cover can be configured to include one or more elements of an anchoring system, as described in U.S. Patent Application Publication No. 2010/0179498, entitled "Reusable Wearable Absorbent Articles with Anchoring Systems," and filed on Jan. 14, 2010, which is incorporated herein by reference. As an additional example, a launderable outer cover can be configured to include one or more elements of an anchoring system, as described in U.S. Patent Application Publication No. 2010/0179502 A1, entitled "Reusable Wearable Absorbent Articles with Anchoring Subsystems," and filed on Jan. 14, 2010, which is incorporated herein by reference.

The outer cover may comprise structures to protect the fastening elements during washing (e.g. protective flaps to cover the hooks or areas adjacent the hooks where the fastener may be temporarily affixed). The absorbent core can be connected to the outer cover by any kind of mechanism, such as pockets, cuffs, straps, loops, hook and loop type fasteners, or fasteners of any type, which can be added onto the outer cover and/or the absorbent core. The outer cover may comprise macro fasteners or any other fastening systems as known in the art. The leg and waist band constructions may be single materials, laminates, etc. The leg and waist bands may be affixed to inner layer only or to outer layer only.

In various alternate embodiments, the exemplary launderable outer cover can be varied in numerous other ways with additional and/or alternate materials, structures, configurations, and assembly methods, as will be understood by one of skill in the art.

Launderable outer cover materials may include any natural or synthetic materials known in the diaper, pant, underwear, performance clothing, sport clothing, or general clothing or textile art. These materials may include natural materials such as cotton, wool, bamboo, hemp, silk, rayon, and the like, as well as blends of these materials with synthetic fibers. Exemplary synthetic materials suitable for use in launderable outer covers may include polyester, nylon, Lycra, Spandex, or other elastomers, breathable waterproof materials such as GORE-TEX® (W. L. Gore & Associates, Inc., Elkton, Md.), fabrics comprising microencapsulated phase-change polymer materials such as Outlast ComforTemp fabrics (Outlast Technologies, Boulder, Colo.—see U.S. Pat. No. 6,514,362 and U.S. Pat. No. 6,207,738 for example), COOLMAX® (INVISTA, Wichita, Kans.), and the like. These materials preferably include at least one fiber-based material, such as a fabric or woven or nonwoven web. However, the outer covers may additionally comprise a film layer to provide enhanced liquid penetration resistance and/or elastic properties to the outer cover. Elastic properties can be added or enhanced via the addition of other materials to the outer cover, including elastic strands, bands, scrims, and the like. Launderable materials may be formed in any known weave or fabric form, including birdseye fabric, terry, fleece, flannel, knits, stretch knits, sherpa, suedecloth, microfleece, satin, velour, Burley knits, and Polartec® Windpro® (Polartec, LLC, Lawrence, Mass.). Knitted textiles, which may be more inherently stretchable and elastic than woven or nonwoven materials, may impart better fit, comfort and/or appearance to the outer cover. Incorporation of fibers of spandex or other elastomer also may also enhance stretchability and elasticity, and thereby impart better fit, comfort and/or appearance to the outer cover, than textiles not including such elastomeric fibers.

Specific suitable examples for launderable outer cover materials include jersey knits of blends of: rayon (93%) and spandex (7%) fibers; modal (94%) and spandex (6%) fibers; cotton and spandex fibers; and bamboo and spandex fibers. Materials that have stretch capability of equal to or greater than about 30%, or 50%, or 100%, or 150%, or even 200% may be desired. Suitable examples of materials may have basis weights of about 0.09-0.15 gram/in.2 per layer, or other basis weights.

Launderable outer cover materials may be selected to impart desired comfort, appearance and performance to a wearable absorbent article. In some circumstances it may be desired to select launderable outer cover materials which are sufficiently inexpensive to allow for disposal, if soiled extensively or damaged, with minimized issues of cost or conscience.

It is contemplated that any launderable outer cover disclosed herein can be used with any embodiment of a wearable absorbent article disclosed herein. The exemplary launderable outer cover can also be adapted for use in a pant type wearable absorbent article.

Exemplary Laundering Resistant Outer Cover

Following is a description of an exemplary laundering resistant outer cover for use in a front fastenable wearable absorbent article. The exemplary launderable outer cover includes a tri-laminate comprising two extensible nonwoven materials and an elastically stretchable film sandwiched in between the nonwovens. The first extensible nonwoven forms the garment-facing side of the outer cover, while the second extensible nonwoven forms the wearer-facing side of the outer cover. The first extensible nonwoven is a 27 gsm HEC nonwoven, such as Excell Style 382D, available from Fiberweb/BBA. The elastically stretchable film comprises a 27 gsm Vistamaxx film (the resin of which is available from Exxon-Mobil) with a polyethylene skin layer of about 5 gsm. The second extensible nonwoven is a 22 gsm nonwoven, such as Sofspan 200 available from Fiberweb France.

The film and the second nonwoven are extrusion bonded together to form a bilaminate. The bilaminate is available as material M18-2038C from Clopay Corp. The first nonwoven is adhesively bonded to the film side of the bilaminate via 0.0006 g/in2 of 2031 spiral adhesive available from Bostik, to form the tri-laminate. The outer cover also includes an anchoring band, disposed within the tri-laminate. The anchoring band is a strip of elastomer film, about 25 mm wide, disposed in the back waist region of the outer cover, oriented parallel to the lateral centerline of the outer cover and extending from the fastener on one side of the outer cover to the fastener on the other side of the outer cover. The trilaminate outer cover is then mechanically activated (i.e., incrementally stretched in a lateral direction) using a ringrolling process. In the ringrolling process, the ringroll tooth pitch is 0.100" and the depth of engagement is 0.158".

As an example, a laundering resistant cover can be configured to include one or more elements of an anchoring system, as described in U.S. Patent Application Publication No. 2010/0179498 A1, entitled "Reusable Wearable Absorbent Articles with Anchoring Systems," and filed on Jan. 14, 2010, which is incorporated herein by reference. As an additional example, a laundering resistant cover can be configured to include one or more elements of an anchoring system, as described in U.S. Patent Application Publication No. 2010/179502 A1, entitled "Reusable Wearable Absorbent Articles with Anchoring Subsystems," and filed on Jan. 14, 2010, which is incorporated herein by reference.

This exemplary laundering resistant outer cover is intended as a non-limiting example. In alternate embodiments, the exemplary laundering resistant outer cover can be varied in numerous ways with additional and/or alternate materials, structures, configurations, and assembly methods, as will be understood by one of skill in the art.

Outer covers that are laundering resistant may still be sufficiently inexpensive to allow them to be disposed without issues of cost or conscience if soiled extensively or damaged. Laundering resistant outer cover materials may include any of the materials described herein, including one or more materials contemplated for use in launderable or disposable outer covers. If materials for use in launderable outer covers are selected, typically less expensive, lower quality (e.g., lower basis weight, less optimal fiber quality) versions may be employed, to form outer covers that are laundering resistant. If materials for use in disposable articles (e.g. disposable diapers) are selected, higher basis weights and/or quality of materials may be appropriate. Blends or laminates of such materials are also contemplated for laundering resistant outer covers.

As an example, a disposable wearable absorbent article design can be modified to make the article laundering resistant. For instance, a wearable absorbent article constructed as described in US patent application publication number 20080312617, entitled "Disposable Absorbent Article with Substantially Continuous Distributed Absorbent Particulate Polymer Material and Method," filed on Dec. 18, 2008, which is hereby incorporated by reference, can be modified by removing the absorbent core, and modifying and/or replacing one or more of the remaining components of the article to make the article more robust and thus laundering resistant.

Alternatively, or in combination, the various component materials of laundering resistant outer covers may be combined using less labor intensive, but less durable, means, such as adhesive or mechanical or thermal bonds (e.g., vs. sewing). Further, the construction of a material, can affect the strength of the material and its ability to withstand degradation when subjected to wash cycles. For example, the type, strength, and degree of bonding in a material can affect the strength of the material, which may then affect whether or not the material is launderable or laundering resistant.

For outer covers that are laundering resistant, materials may include any natural or synthetic nonwoven web and/or film materials known in the diaper or pant arts. Laundering resistant materials of which an outer cover may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of an outer cover. In addition to these materials, films, such as polyolefin films (microporous or non-microporous) can also be used in a laundering resistant outer cover.

Non-limiting examples of fibers, nonwovens and laminates of nonwovens and films that might be considered for use as laundering resistant outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587.

Laundering resistant outer cover materials also may be selected to impart desired comfort, appearance and performance to the outer cover. In some circumstances it also may be desired to select laundering resistant outer cover materials which are sufficiently inexpensive to allow for disposal, if soiled extensively or damaged, with minimized issues of cost or conscience.

The outer cover also, or additionally, may include a laminated or substantially separate film layer, which may be elastic, to provide enhanced liquid penetration resistance and/or elastic properties. Elastic properties also can be added or enhanced via the addition of other materials to the outer cover in layer, band or strip fashion, including elastic strands, bands, scrims, foams, and the like. A film layer may be laminated with a launderable material or laundering resistant material. A film layer may include an elastomer based on KRATON (a product of Kraton Polymers U.S., LLC, Houston, Tex.); VISTAMAXX available from ExxonMobil Chemical Company, Houston, Tex.; FLEXAIRE, EXTRAFLEX or FABRIFLEX (products of Tredegar Film Products Corporation, Richmond, Va.), and various latex-free elastomeric sheets available from Fulflex Elastomerics Worldwide (Greenville, Tenn.).

Inclusion of an elastomeric material, either as a fibrous component of a cloth or nonwoven layer, or as a film layer, provides for improved stretchability and elasticity where it may be deemed useful to accommodate the wearer's anatomy and movements, such as over the wearer's buttocks and/or around the waist areas, and improved fit and comfort. Additionally, where a film layer may be included, it may impart additional liquid containment capability to the outer cover. A film layer may include a film that is substantially liquid impermeable, but vapor permeable, so as to provide breathability and reduce humidity within the outer cover while it is being worn, reducing chances for overhydration of the skin where liquid containment capability is desired.

Layers or elements of the outer cover may be joined to each other via any means known in the diaper or clothing art, including, for example, adhesives, mechanical bonding, ultrasonic bonding, sewing, stitching, serging, edging, and the like.

It is contemplated that any laundering resistant outer cover disclosed herein can be used with any embodiment of a wearable absorbent article disclosed herein. The exemplary laundering resistant outer cover can also be added for use in a pant type wearable absorbent article.

Reusable outer covers may need to be washed prior to reuse if they become soiled by bodily exudates, such as urine, feces, or sweat, or by environmental contaminants. Caregivers may also choose to wash the outer cover to freshen it, remove malodors, add a pleasant fragrance, or generally restore its shape, neatness, and/or appearance. In general, caregivers may expect more expensive outer covers to be washable a greater number of wash cycles without significant deterioration of physical properties or appearance of the outer cover. Laundering resistant outer covers may be generally constructed of less expensive materials than launderable outer covers and, therefore, expected to deteriorate more rapidly with increasing number of washing cycles, e.g., deteriorate beyond the point of usefulness after fewer washing cycles, than launderable outer covers.

While the aesthetic appearance of the outer cover after multiple wash cycles is important to some caregivers' perceived value of the outer cover, the acceptable appearance is highly dependent on individual preference. Also, even outer covers with a more "worn" appearance may be acceptable to wear in certain places (e.g., home) or usage situations (e.g., overnight or when child has an illness such as diarrhea). Therefore, it is more critical that laundering resistant outer covers and launderable outer covers be capable of their intended use after at least one wash cycle and 10 wash cycles, respectively.

As loads from wearer exudates or motion tend to move a wearable absorbent article down on a wearer, embodiments of the present disclosure can help prevent wearable absorbent articles from sagging and/or slipping down on a wearer. A wearable absorbent article can include an anchoring system. In various embodiments, an anchoring system can be configured to collect at least some of the loads acting upon the article and/or distribute them to a location on the wearer's body capable of supporting the loads. The anchoring system can also be configured to anchor itself to a body of a wearer. In this way, the anchoring system can balance at least some of the collected loads with holding forces obtained from the anchoring system. By balancing the collected loads with the obtained holding forces, the anchoring system can at least assist in holding the wearable absorbent article in place on a wearer.

An anchoring system can be configured to collect loads acting upon a wearable absorbent article, to anchor itself to a body of a wearer, and to balance the collected loads with holding forces obtained from the anchoring. Throughout the present disclosure, the term "anchored" refers to a configured relationship between part, or parts, or all of an anchoring system in a wearable absorbent article and part, or parts, or all of a body of a wearer, while the article is worn by the wearer. Where an anchoring system is anchored to a portion of a body of a wearer, at least part of an anchoring element is in direct and/or indirect contact with the portion of the body and the anchoring system is configured to at least reduce and/or prevent relative movement between the anchoring element and the portion, while the article is worn by the wearer.

An anchoring system can be anchored to a body of a wearer with one or more anchoring elements of the anchoring system configured to contact one or more of various parts of a body of a wearer. For example, an anchoring system can be at least partially anchored by wrapping one or more anchoring elements at least partway around a front, back, and/or side of a body of a wearer, thus creating friction and/or reaction forces.

A part of the body with a relatively smaller radius of curvature can, in some embodiments, provide greater friction forces, since an anchoring element can tend to wrap around such parts more tightly. This is due to the physics of a flexible material that is wrapped around a curved surface and placed under tension. In this scenario, as a tensile force places the flexible material under tension, the flexible material exerts a normal force perpendicular to and inward on the curved surface. According to the basic Capstan formula, the normal force is proportional to the tensile force divided by the radius of the curved surface. Thus, at a given tensile force as the radius becomes smaller the normal force becomes larger.

Also as an example, an anchoring system can be at least partially anchored by setting one or more anchoring elements on, around, and/or above one or more protruding portions of a body of a wearer, thus creating friction and/or reaction forces. A part of the body with a relatively larger horizontal protrusion can, in some embodiments, provide greater reaction forces, since an anchoring element can tend to hang and/or ride on such parts more securely (i.e., there is an upward component to the reaction force from the body that can support a load).

In order to collect loads, anchor itself to a body of a wearer, and balance various forces, an anchoring system can be configured to include one or more anchoring elements. In some embodiments, an anchoring element can be an elongated anchoring element configured to carry tension. Anchoring elements can follow various pathways on surfaces within a wearable absorbent article and/or on external surfaces of a body of a wearer of the wearable absorbent article in which the anchoring system is included. The shapes of these surfaces can affect the shapes of the pathways. The shapes of the pathways can, in turn, affect configurations of anchoring elements.

In an anchoring system of a wearable absorbent article, one or more anchoring elements can be configured to at least assist in anchoring the anchoring system to the body. Some anchoring elements can receive collected loads from one or more elements of the wearable absorbent article, such as a chassis, a fastener, a leg cuff, or another anchoring element. Some anchoring elements can transmit loads and/or forces in an anchoring system. Some anchoring elements can provide holding forces through contact with the body of a wearer. As a result, by balancing loads and forces, anchoring systems can at least assist in holding a wearable absorbent article in place on a wearer.

An anchoring element can be configured in various forms. An anchoring element can be made from any material suitable for carrying tensions in an anchoring system. Part, or parts, or substantially all, or all of an anchoring element can include one or more of various elastic, inelastic, extensible, inextensible, stretchable, and/or non-stretchable material(s) and/or any other suitable material(s) and/or combinations of any of these materials. An anchoring element pathway can be a unitary, continuous pathway, or can be formed by a number of discrete elements and/or separate areas disposed along a pathway. Part, or parts, or substantially all, or all of an anchoring element can be straight, curved, angled, segmented, or other shapes, or combinations of any of these shapes. In some embodiments, an anchoring element can include a number of elements, such as fasteners. Part, or parts, or substantially all, or all of an anchoring member can be structurally associated with, and/or joined to, and/or attached to, and/or durably attached to, and/or refastenably attached to, and/or embedded in, and/or integral with one or more other elements (such as an outer cover and/or a waist cover an/or an absorbent core) of a wearable absorbent article. When an anchoring member is embedded in or integral with one or more other elements, the anchoring member forms a distinct and recognizable pathway within that structure. For example, when an anchoring member is integral with an outer cover, the anchoring member can form a pathway with a higher modulus of elasticity than areas of the outer cover surrounding the pathway. As used herein, the term "joined" refers to configurations wherein an element is directly secured to another element and to configurations wherein an element is indirectly secured to another element by connecting the element to one or more intermediate members, which are, in turn connected to the other element.

An anchoring element can be any suitable width or thickness. For example, an anchoring element can be from 5 mm to about 100 mm wide or any width within that range. The width and/or thickness of an anchoring element can be substantially or completely uniform over one or more parts of the anchoring element or over the entire length of the anchoring element, or can vary over the length of the anchoring element. In some embodiments, an anchoring element can have a substantially uniform width of about 10 mm, about 20 mm, about 30 mm, about 40 mm, or about 50 mm. Throughout the present disclosure, unless otherwise stated, the width of an anchoring element is measured at a particular point on the anchoring element's pathway, as the largest overall dimension across the pathway, from one side edge of the pathway to the other side edge of the pathway, in a direction perpendicular to the anchoring element's centerline.

One kind of anchoring element is an anchoring band. An anchoring band is an anchoring element that includes one or more physical, tension-carrying elements and/or areas disposed along a defined anchoring band pathway in a wearable absorbent article. An anchoring band can be configured to transmit force in tension from one end to the other and to have sufficient strength to carry such tension in an anchoring system. In some embodiments, a portion of an absorbent core of a wearable absorbent article can form an implied anchoring band, by being structurally configured to carry increased tension across that portion. In various embodiments, an anchoring band can at least partially encircle a lower torso of the body of the wearer, for example in the back portion of the article.

Another kind of anchoring element is a load distribution element (LDE). An LDE is a type of anchoring band that directs and/or distributes loads in an anchoring system of a wearable absorbent article. An LDE can receive at least some collected loads by being joined to one or more other elements of the wearable absorbent article, such as an absorbent core. Also, an LDE can direct and/or distribute such loads by being joined to one or more anchoring elements of an anchoring system, such as a CAM or anchoring band. In various embodiments, LDEs can be configured to direct and/or distribute part, or parts, or substantially all, or all of loads from an absorbent core of a wearable absorbent article.

Yet another kind of anchoring element is a spine. A spine is a type of anchoring band that helps support an absorbent core in an anchoring system of a wearable absorbent article. A spine includes one or more physical, tension-carrying elements and/or areas disposed along a defined spine pathway in a wearable absorbent article. A spine is oriented either substantially or completely laterally or substantially or completely longitudinally. A substantial portion of a spine pathway passes through an area of an absorbent core of a wearable absorbent article. In some embodiments, substantially all or all of a spine can be contained within an area of an absorbent core.

Even another kind of anchoring element is a circumferential anchoring member (CAM). A circumferential anchoring member (CAM) is an anchoring element that includes one or more physical, tension-carrying elements and/or areas disposed along a defined CAM pathway in a wearable absorbent article. A CAM pathway generally follows a curved surface within a wearable absorbent article or on a body of a wearer. A CAM pathway at least partially encircles a lower torso of the body of the wearer. In some embodiments, a CAM pathway can substantially or completely encircle the lower torso of the body of the wearer. While a CAM may follow a curved pathway when the article is being worn by a wearer, the CAM may appear substantially or completely linear when viewed in an absorbent article laid out flat.

The embodiments of FIGS. 1A through 5B describe various anchoring systems for use in wearable absorbent articles, including reusable wearable absorbent articles and disposable wearable absorbent articles. These anchoring systems can be configured with one or more CAMs, anchoring bands, LDEs, spines, and/or other anchoring elements, in various ways, as described herein. Each of these anchoring systems can be configured in a wearable absorbent article to anchor an absorbent core to a wearer. In various embodiments, each of these anchoring systems can be configured in a wearable absorbent article to substantially decouple an outer cover from the loads from an absorbent core. In various embodiments, each of these anchoring systems can be configured in a wearable absorbent article to carry part, or parts, or substantially all, or all of the loads from an absorbent core.

FIG. 1A illustrates a plan view of an inside (wearer-facing side) of a front fastenable wearable absorbent article 101, which includes an anchoring system 130. The front fastenable wearable absorbent article 101 can be configured as a reusable wearable absorbent article or as a disposable wearable absorbent article.

While the present disclosure refers to front fastenable wearable absorbent articles, the present disclosure also contemplates alternate embodiments of wearable absorbent articles, as described herein, wherein the wearable absorbent articles are rear-fastenable or side-fastenable. Thus, each embodiment of a wearable absorbent article of the present disclosure that is described as front fastenable can also be configured to be rear fastenable, etc., as will be understood by one of ordinary skill in the art.

In FIG. 1A, a longitudinal centerline 113 and a lateral centerline 117 provide lines of reference for referring to relative locations of parts of the wearable absorbent article 101. When a first part is nearer to the longitudinal centerline 113 than a second part, the first part can be considered laterally inboard 112 to the second part. Similarly, the second part can be considered laterally outboard 114 from the first part. When a third part is nearer to the lateral centerline 117 than a fourth part, the third part can be considered longitudinally inboard 116 to the fourth part. Similarly, the fourth part can be considered longitudinally outboard 118 from the third part. FIG. 1A includes arrows indicating relative directions for laterally inboard 112, laterally outboard 114, longitudinally inboard 116, and longitudinally outboard 118, with respect to the wearable absorbent article 101. Throughout the present disclosure, unless otherwise stated, a reference to a longitudinal dimension, measurement, line, or direction refers to a dimension, measurement, line, or direction substantially or completely parallel to the longitudinal centerline 113, and a reference to a lateral dimension, measurement, line, or direction refers to a dimension, measurement, line, or direction substantially or completely parallel to the lateral centerline 117.

The wearable absorbent article 101 includes a chassis 121, defining the outermost edges of the article 101. The chassis 121 includes a front 123 and a back 125. The front 123 is a portion of the wearable absorbent article 101 disposed generally proximate to and/or below the belly of a wearer, when the wearable absorbent article 101 is worn by the wearer. A reference to the "front" can mean the front itself, part, or parts, or substantially all, or all of an element in the front, and/or a disposition in the front, depending on the context of the reference. The back 125 is a portion of the wearable absorbent article 101 disposed generally proximate to and/or below the back of a wearer, when the wearable absorbent article 101 is worn by the wearer. A reference to the "back" can mean the back itself, part, or parts, or substantially all, or all of an element in the back, and/or a disposition in the back, depending on the context of the reference. The lateral centerline 117 of the wearable absorbent article 101 forms a boundary between the front 123 and the back 125. The front and back terminology described above is used for wearable absorbent articles throughout the present disclosure, unless otherwise indicated. The wearable absorbent article 101 also includes an absorbent core 127 extending from the front 123 to the back 125.

The wearable absorbent article 101 further includes a side 152, a side ear 153, and fasteners 154. The side 152 is disposed in the back 125, laterally outboard from a narrowest portion of the chassis 121. Although the side 152 is illustrated as to the right of the longitudinal centerline 113, the wearable absorbent article 101 also includes another side, of the same configuration, to the left of the longitudinal centerline 113. The side 152 includes side ear 153, which is the portion of the wearable absorbent article 101 laterally extending outward from the longitudinal side of the chassis 121, as illustrated by the phantom line, which is provided for reference. In various embodiments, part, or parts, or substantially all, or all of a side ear may be formed by a portion of a chassis or may be formed by a separate element attached to a chassis. The wearable absorbent article 101 includes a second side ear as part of the other side. Each of the side ears 153 includes a fastener 154, for fastening the back 125 to the front 123. In various embodiments, in addition to the elements described and illustrated herein, the wearable absorbent article 101 may also include one or more of: a front waistband, a rear waistband, and legbands.

The anchoring system 130 includes a first back CAM 131 disposed in the back 125, back LDEs 133 disposed in the back 125, a first front CAM 141 disposed in the front 123, front LDEs 143 disposed in the front 123, and a spine 135, 145. The spine 135, 145 includes a back portion of the spine 135 disposed in the back 125 and a front portion of the spine 145 disposed in the front 123.

The first back CAM 131 is disposed longitudinally inboard to and offset from the longitudinally outboard back edge of the chassis 121. The first back CAM 131 is also disposed longitudinally inboard to and offset from the longitudinally outboard back edge of the absorbent core 127. The first back CAM 131 is joined to one fastener 154 and extends laterally from that one fastener 154, laterally through a first portion of the back 125, laterally across, below, and joined to a back portion of the absorbent core 127, laterally through a second portion of the back 125, and laterally to the other fastener 154, joining to that other fastener 154. The first back CAM 131 can be configured within the wearable absorbent article 101 in any manner described herein. The first back CAM 131 is considered a CAM because, when the wearable absorbent article 101 is worn by a wearer, the first back CAM 131 at least partially encircles the wearer.

In a first alternate embodiment, part, or parts, or substantially all, or all of the first back CAM 131 could be disposed proximate to the longitudinally outboard back end of the absorbent core 127. In a second alternate embodiment, part, or parts, or substantially all, or all of the first back CAM 131 could be disposed longitudinally outboard from the longitudinally outboard back end of the absorbent core 127. In a third alternate embodiment, part, or parts, or substantially all, or all of the first back CAM 131 could be disposed proximate to the longitudinally outboard back edge of the chassis 121. In a fourth alternate embodiment, part or parts of the first back CAM 131 could follow one or more alternate pathways in either or both of the sides 152 or either or both of the side ears 153. In a fifth alternate embodiment, part or parts of the first back CAM 131 could connect to one or more additional anchoring elements, as described herein. In a sixth alternate embodiment, the first back CAM 131 may not join to one or both of the fasteners 154. In a seventh alternate embodiment, part, or parts, or substantially all, or all of the first back CAM 131 may extend through or above the absorbent core 127. In an eighth alternate embodiment, part, or parts, or substantially all, or all of the first back CAM 131 may not be joined to the absorbent core 127. In any of these alternate embodiments, part, or parts, or substantially all, or all of the first back CAM 131 could be omitted. Also, in any of these alternate embodiments, one or more anchoring bands could be used along part, or parts, or substantially all, or all of the pathway of the first back CAM 131. Further, any of these alternate embodiments could be combined in whole or in part to create additional alternate embodiments.

There are two back LDEs 133, one on each side of the longitudinal centerline 113. For the back LDE 133 to the right of the longitudinal centerline, one end of the back LDE 133 connects to the back portion of the spine 135 at a location longitudinally offset from the lateral centerline 117. A portion of that back LDE 133 is disposed below a back portion of the absorbent core 127, and is joined to that portion. That back LDE 133 extends from the back portion of the spine 135, laterally and longitudinally outward, and connects to the first back CAM 131 at a location proximate to the side 152. The first back LDE 133 is considered an LDE because, when the wearable absorbent article 101 is worn by a wearer, the first back LDE 133 is configured to direct and/or distribute at least part of the load from the absorbent core 127 to the first back CAM 131. The back LDE 133 on the left is configured in the same way, though mirrored by the longitudinal centerline 113. Each back LDE 133 can be configured within the wearable absorbent article 101 in any manner described herein, including any of the alternative embodiments.

In a first alternate embodiment, a back LDE 133 could connect to the back portion of the spine 135 at a location at or proximate to the lateral centerline 117. In a second alternate embodiment, a back LDE 133 may not connect to the back portion of the spine 135, but may end at a location offset from the longitudinal centerline 113, within the area of the back portion of the absorbent core 127. In a third alternate, a back LDE 133 could connect to the first back CAM 131 at a location at or proximate to the longitudinal centerline 113. In a fourth alternate, a back LDE 133 could connect to the first back CAM 131 within the side ear 152, within the side ear 153, and/or proximate to the fastener 154. In a fifth alternate embodiment, part or parts of a back LDE 133 could follow one or more alternate pathways in either or both of the sides 152 or either or both of the side ears 153. In a six alternate embodiment, part or parts of a back LDE 133 could connect to one or more additional anchoring elements, as described herein. In a seventh alternate embodiment, part, or parts, or substantially all, or all of a back LDE 133 may extend through or above the absorbent core 127. In an eighth alternate embodiment, part, or parts, or substantially all, or all of a back CAM 133 may not be joined to the absorbent core 127. In any of these alternate embodiments, part, or parts, or substantially all, or all of either or both back LDEs 133 could be omitted. Also, in any of these alternate embodiments, one or more anchoring bands could be used along part, or parts, or substantially all, or all of the pathway of a back LDE 133. Further, any of these alternate embodiments could be combined in whole or in part to create additional alternate embodiments.

The first front CAM 141 is disposed longitudinally inboard to and offset from the longitudinally outboard front edge of the chassis 121. The first front CAM 141 is also disposed longitudinally inboard to and offset from the longitudinally outboard front edge of the absorbent core 127. The first front CAM 141 begins in one side, extends laterally from one longitudinal side edge of the chassis 121, laterally through a first portion of the front 123, laterally across, below, and joined to a front portion of the absorbent core 127, laterally through a second portion of the front 123, and ends in another side at another longitudinal side edge of the chassis 121. The first front CAM 141 can be configured within the wearable absorbent article 101 in any manner described herein. The first front CAM 141 is considered a CAM because, when the wearable absorbent article 101 is worn by a wearer, the first front CAM 141 at least partially encircles the wearer. When the wearable absorbent article 101 is worn by a wearer, the first front CAM 141 and the first back CAM 131, together, can be considered a single CAM that completely encircles the wearer.

In a first alternate embodiment, part, or parts, or substantially all, or all of the first front CAM 141 could be disposed proximate to the longitudinally outboard front end of the absorbent core 127. In a second alternate embodiment, part, or parts, or substantially all, or all of the first front CAM 141 could be disposed longitudinally outboard from the longitudinally outboard front end of the absorbent core 127. In a third alternate embodiment, part, or parts, or substantially all, or all of the first front CAM 141 could be disposed proximate to the longitudinally outboard front edge of the chassis 121. In a fourth alternate embodiment, part or parts of the first front CAM 141 could follow one or more alternate pathways proximate to either or both of the longitudinal sides, similar to the embodiments described in connection with FIG. 14B. In a fifth alternate embodiment, part or parts of the first front CAM 141 could connect to one or more additional anchoring elements, as described herein. In a sixth alternate embodiment, part, or parts, or substantially all, or all of the first front CAM 141 may extend through or above the absorbent core 127. In a seventh alternate embodiment, part, or parts, or substantially all, or all of the first front CAM 141 may not be joined to the absorbent core 127. In any of these alternate embodiments, part, or parts, or substantially all, or all of the first front CAM 141 could be omitted. Also, in any of these alternate embodiments, one or more anchoring bands could be used along part, or parts, or substantially all, or all of the pathway of the first front CAM 141. Further, any of these alternate embodiments could be combined in whole or in part to create additional alternate embodiments.

There are two front LDEs 143, one on each side of the longitudinal centerline 113. The front LDEs 143 are configured in the same way as the back LDEs 133, though mirrored by the lateral centerline 117, and except for the differences between a back and a front of a front fastenable wearable absorbent article. Each front LDE 143 can be configured within the wearable absorbent article 101 in any manner described herein, including any of the alternative embodiments.

The back portion of the spine 135 connects to the first back CAM 131 and to the front portion of the spine 145. The back portion of the spine 135 is below and joined to a back portion of the absorbent core 127. The front portion of the spine 145 connects to the back portion of the spine 135 and to the first front CAM 141. The front portion of the spine 145 is below and joined to a front portion of the absorbent core 127. The spine 135, 145 is laterally centered on the wearable absorbent article 101. The spine 135, 145 can be configured within the wearable absorbent article 101 in any manner described herein.

In a first alternate embodiment, part, or parts, or substantially all, or all of the back portion of the spine 135 and/or part, or parts, or substantially all, or all of the front portion of the spine 145 could be disposed offset from the longitudinal centerline 113 and/or proximate to a laterally outboard side of the absorbent core 127. In a second alternate embodiment, part, or parts, or substantially all, or all of the back portion of the spine 135 and/or part, or parts, or substantially all, or all of the front portion of the spine 145 could be disposed outside of the area of the absorbent core 127. In a third alternate embodiment, part or parts of the back portion of the spine 135 could connect to the first back CAM 131 at one or more additional and/or alternate locations, and/or part or parts of the front portion of the spine 145 could connect to the first front CAM 141 at one or more additional and/or alternate locations. In a fourth alternate embodiment, part or parts of the back portion of the spine 135 and/or part or parts of the front portion of the spine 145 could connect to one or more additional anchoring elements, as described herein. In a fifth alternate embodiment, the wearable absorbent article 101 could include two or more spines. In a sixth alternate embodiment, part, or parts, or substantially all, or all of the back portion of the spine 135 and/or part, or parts, or substantially all, or all of the front portion of the spine 145 may not be joined to the absorbent core 127. In any of these alternate embodiments, part, or parts, or substantially all, or all of the pathway of the back portion of the spine 135 and/or part, or parts, or substantially all, or all of the pathway of the front portion of the spine 145 could be omitted. In any of these alternate embodiments, one or more anchoring bands could be used along part, or parts, or substantially all, or all of the pathway of the back portion of the spine 135 and/or the front portion of the spine 145. Further, any of these alternate embodiments could be combined in whole or in part to create additional alternate embodiments.

Additionally, any of the embodiments of the front 123 of the wearable absorbent article 101 could be combined with any of the embodiments of a back of any of the front fastenable wearable absorbent articles, as disclosed herein. Further, any of the embodiments of the back 125 of the wearable absorbent article 101 could be combined with any of the embodiments of a front of any of the front fastenable wearable absorbent articles, as disclosed herein, to create further alternate embodiments.

Figure 1B:
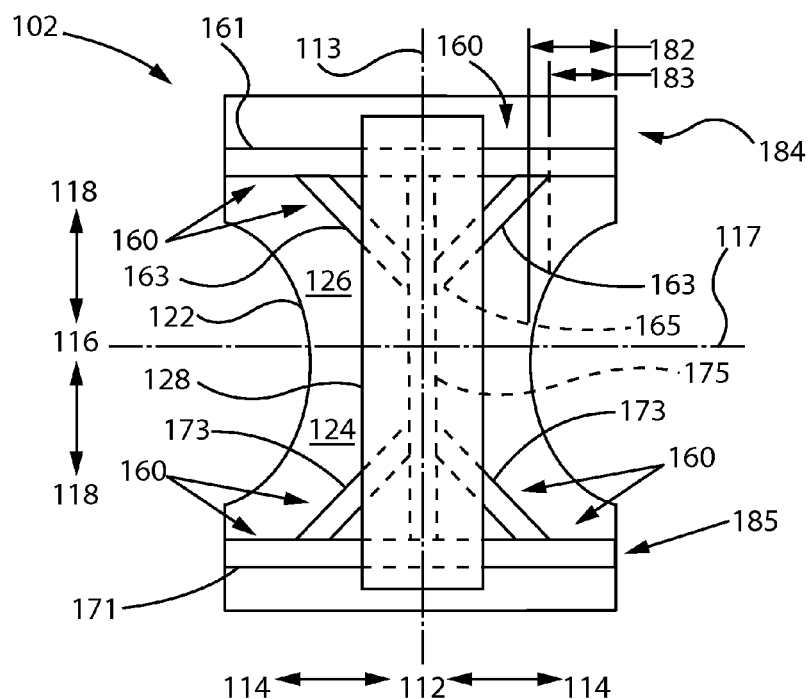
FIG. 1B illustrates a plan view of an inside of a pant type wearable absorbent article, which includes a first anchoring system.

FIG. 1B illustrates a plan view of an inside (wearer-facing side) of a pant type wearable absorbent article 102, which includes an anchoring system 160. The pant type wearable absorbent article 102 can be configured as a reusable wearable absorbent article or as a disposable wearable absorbent article.

Throughout the present disclosure, a reference to a pant type wearable absorbent article can refer to an embodiment that is fastenable or to an embodiment without fasteners. A reference to a pant type wearable absorbent article can also refer to an embodiment of an article with one or more waist and/or leg openings that are preformed (i.e. formed during manufacture of the article) or to an embodiment of an article with waist and leg openings that are not preformed. Thus, each embodiment of an absorbent article of the present disclosure that is described as pant type can be configured in any of these ways, as will be understood by one of ordinary skill in the art.

In FIG. 1B, a longitudinal centerline 113 and a lateral centerline 117 provide lines of reference for referring to laterally inboard 112, laterally outboard 114, longitudinally inboard 116, and longitudinally outboard 118 relative locations of parts of the wearable absorbent article 102. The wearable absorbent article 102 includes a chassis 122, defining the outermost edges of the article 102. The chassis 122 includes a front 124 and a back 126. The wearable absorbent article 102 also includes an absorbent core 128 extending from the front 124 to the back 126.

The wearable absorbent article 102 further includes a side 182, a portion of a side panel 183, and side panel connections 184, 185. The side 182 is disposed in the back 126, laterally outboard from a narrowest portion of the chassis 122. Although the side 182 is illustrated as to the right of the longitudinal centerline 113, the wearable absorbent article 102 also includes another side, of the same configuration, to the left of the longitudinal centerline 113. The side 182 includes the portion of the side panel 183, which is the portion of the wearable absorbent article laterally extending outward from the longitudinal side of the chassis 122, as illustrated by the phantom line, which is provided for reference. In various embodiments, part, or parts, or substantially all, or all of the portion of a side panel may be formed by a portion of a chassis or may be formed by a separate element attached to a chassis. The wearable absorbent article 102 includes a second portion of a side panel as part of the other side. The wearable absorbent article 102 also includes portions of side panels in the front. When wearable absorbent article 102 is formed for wearing, each front portion of a side panel connects to a corresponding back portion of a side panel at a side panel connection. On the right side, when the wearable absorbent article 102 is formed for wearing, the side panel connection 184 in the back 126 is joined to the side panel connection 185 in the front 124. The left side is joined in the same way. In various embodiments, in addition to the elements described and illustrated herein, the wearable absorbent article 102 may also include one or more of: a front waistband, a rear waistband, and legbands.

The anchoring system 160 includes a first back CAM 161 disposed in the back 126, back LDEs 163 disposed in the back 126, a first front CAM 171 disposed in the front 124, front LDEs 173 disposed in the front 124, and a spine 165, 175. The spine 165, 175 includes a back portion of the spine 165 disposed in the back 126 and a front portion of the spine 175 disposed in the front 124.

The first back CAM 161 is disposed longitudinally inboard to and offset from the longitudinally outboard back edge of the chassis 122. The first back CAM 161 is also disposed longitudinally inboard to and offset from the longitudinally outboard back edge of the absorbent core 128. The first back CAM 161 begins in one portion of a side panel 183, extends laterally from one longitudinal side edge of the chassis 122, laterally through a first portion of the back 126, laterally across, below, and joined to a back portion of the absorbent core 128, laterally through a second portion of the back 126, and ends in another portion of a side panel at another longitudinal side edge of the chassis 122. The first back CAM 161 can be configured within the wearable absorbent article 102 in any manner described herein. The first back CAM 161 is considered a CAM because, when the wearable absorbent article 102 is worn by a wearer, the first back CAM 161 at least partially encircles the wearer.

In a first alternate embodiment, part, or parts, or substantially all, or all of the first back CAM 161 could be disposed proximate to the longitudinally outboard back end of the absorbent core 128. In a second alternate embodiment, part, or parts, or substantially all, or all of the first back CAM 161 could be disposed longitudinally outboard from the longitudinally outboard back end of the absorbent core 128. In a third alternate embodiment, part, or parts, or substantially all, or all of the first back CAM 161 could be disposed proximate to the longitudinally outboard back edge of the chassis 122. In a fourth alternate embodiment, part or parts of the first back CAM 161 could follow one or more alternate pathways in either or both of the sides 182 or either or both of the portions of side panels 183, as described in connection with FIG. 14B.

In a fifth alternate embodiment, part or parts of the first back CAM 161 could connect to one or more additional anchoring elements, as described herein. In a sixth alternate embodiment, part, or parts, or substantially all, or all of the first back CAM 161 may extend through or above the absorbent core 128. In a seventh alternate embodiment, part, or parts, or substantially all, or all of the first back CAM 161 may not be joined to the absorbent core 128. In any of these alternate embodiments, part, or parts, or substantially all, or all of the first back CAM 161 could be omitted. Also, in any of these alternate embodiments, one or more anchoring bands could be used along part, or parts, or substantially all, or all of the pathway of the first back CAM 161. Further, any of these alternate embodiments could be combined in whole or in part to create additional alternate embodiments.

There are two back LDEs 163, one on each side of the longitudinal centerline 113. The back LDEs 163 are configured in the same way as the back LDEs 133 of the embodiment of FIG. 1A, except for the differences between a pant type wearable absorbent article and a front fastenable wearable absorbent article. Each back LDE 163 can be configured within the wearable absorbent article 102 in any manner described herein, including any of the alternative embodiments.

The first front CAM 171 is disposed longitudinally inboard to and offset from the longitudinally outboard front edge of the chassis 122. The first front CAM 171 is also disposed longitudinally inboard to and offset from the longitudinally outboard front edge of the absorbent core 128. The first front CAM 171 begins in one portion of a side panel, extends laterally from one longitudinal side edge of the chassis 122, laterally through a first portion of the front 124, laterally across, below, and joined to a front portion of the absorbent core 128, and laterally through a second portion of the front 124, and ends in another portion of a side panel at another longitudinal side edge of the chassis 122, The first front CAM 171 can be configured within the wearable absorbent article 102 in any manner described herein. The first front CAM 171 is considered a CAM because, when the wearable absorbent article 102 is worn by a wearer, the first front CAM 171 at least partially encircles the wearer. When the wearable absorbent article 102 is worn by a wearer, the first front CAM 171 and the first back CAM 161, together, can be considered a single CAM that completely encircles the wearer.

In a first alternate embodiment, part, or parts, or substantially all, or all of the first front CAM 171 could be disposed proximate to the longitudinally outboard front end of the absorbent core 128. In a second alternate embodiment, part, or parts, or substantially all, or all of the first front CAM 171 could be disposed longitudinally outboard from the longitudinally outboard front end of the absorbent core 128. In a third alternate embodiment, part, or parts, or substantially all, or all of the first front CAM 171 could be disposed proximate to the longitudinally outboard front edge of the chassis 122. In a fourth alternate embodiment, part or parts of the first front CAM 171 could follow one or more alternate pathways proximate to either or both of the longitudinal sides, similar to the embodiments described in connection with FIG. 14B. In a fifth alternate embodiment, part or parts of the first front CAM 171 could connect to one or more additional anchoring elements, as described herein. In a sixth alternate embodiment, part, or parts, or substantially all, or all of the first front CAM 171 may extend through or above the absorbent core 128. In a seventh alternate embodiment, part, or parts, or substantially all, or all of the first front CAM 171 may not be joined to the absorbent core 128. In any of these alternate embodiments, part, or parts, or substantially all, or all of the first front CAM 171 could be omitted. Also, in any of these alternate embodiments, one or more anchoring bands could be used along part, or parts, or substantially all, or all of the pathway of the first front CAM 171. Further, any of these alternate embodiments could be combined in whole or in part to create additional alternate embodiments.

There are two front LDEs 173, one on each side of the longitudinal centerline 113. The front LDEs 173 are configured in the same way as the front LDEs 143 of the embodiment of FIG. 1A, except for the differences between a pant type wearable absorbent article and a front fastenable wearable absorbent article. Each front LDE 173 can be configured within the wearable absorbent article 102 in any manner described herein, including any of the alternative embodiments.

The back portion of the spine 165 connects to the first back CAM 161 and to the front portion of the spine 175. The back portion of the spine 165 is below and joined to a back portion of the absorbent core 128. The front portion of the spine 165 connects to the back portion of the spine 165 and to the first front CAM 171. The front portion of the spine 175 is below and joined to a front portion of the absorbent core 128. The spine 165, 175 is laterally centered on the wearable absorbent article 102. The spine 165, 175 can be configured within the wearable absorbent article 102 in the same way that the spine 135, 145 is configured within the wearable absorbent article 101 in the embodiment of FIG. 1A, including any alternate embodiments.

Additionally, any of the embodiments of the front 124 of the wearable absorbent article 102 could be combined with any of the embodiments of a back of any of the pant type wearable absorbent articles, as disclosed herein. Further, any of the embodiments of the back 126 of the wearable absorbent article 102 could be combined with any of the embodiments of a front of any of the pant type wearable absorbent articles, as disclosed herein, to create further alternate embodiments.

Figure 1C:
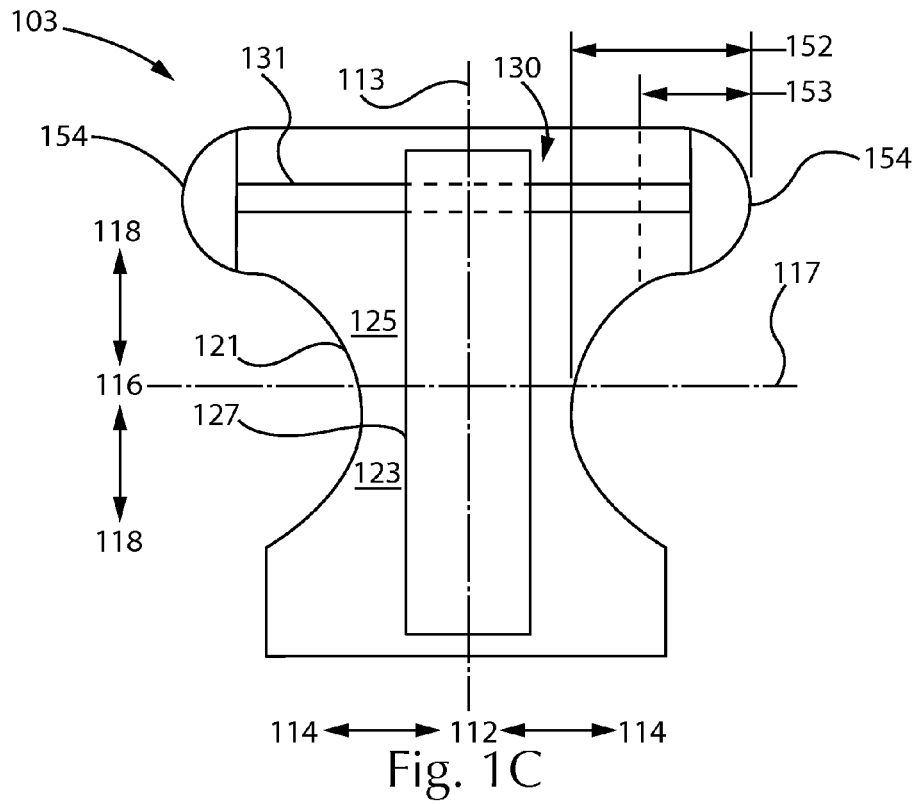
FIG. 1C illustrates a plan view of an inside of a front fastenable wearable absorbent article, which includes a back anchoring band.

FIG. 1C illustrates a plan view of an inside of a front fastenable wearable absorbent article 103. The front fastenable wearable absorbent article 103 is configured in the same way as the front fastenable wearable absorbent article 101 of FIG. 1A, except that the anchoring system 130 consists of the first back CAM 131.

Figure 1D:
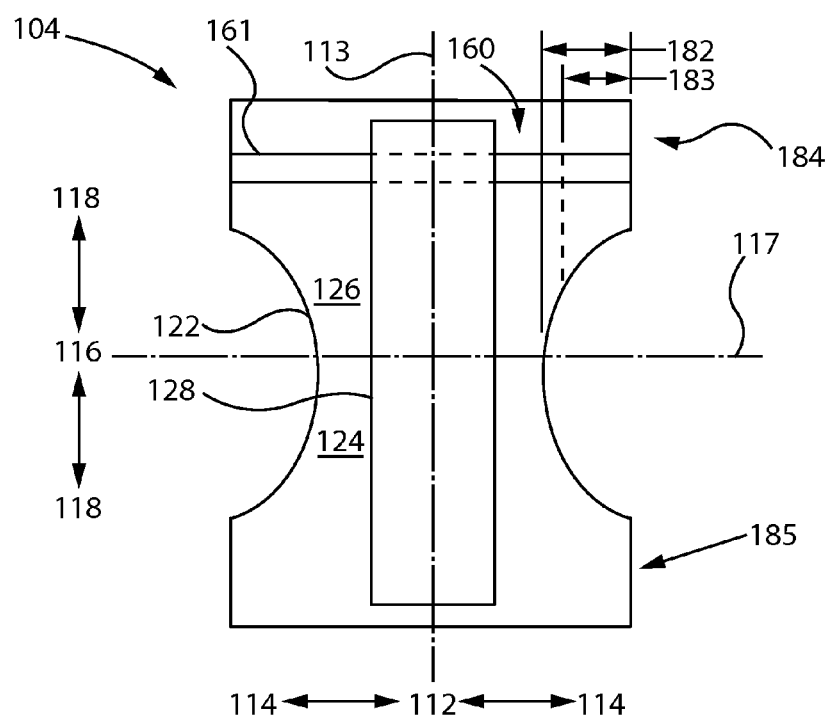
FIG. 1D illustrates a plan view of an inside of a pant type wearable absorbent article, which includes a back anchoring band.

FIG. 1D illustrates a plan view of an inside of a pant type wearable absorbent article 104. The pant type wearable absorbent article 104 is configured in the same way as the pant type wearable absorbent article 102 of FIG. 1B, except that the anchoring system 160 consists of the first back CAM 161.

Figure 2A:
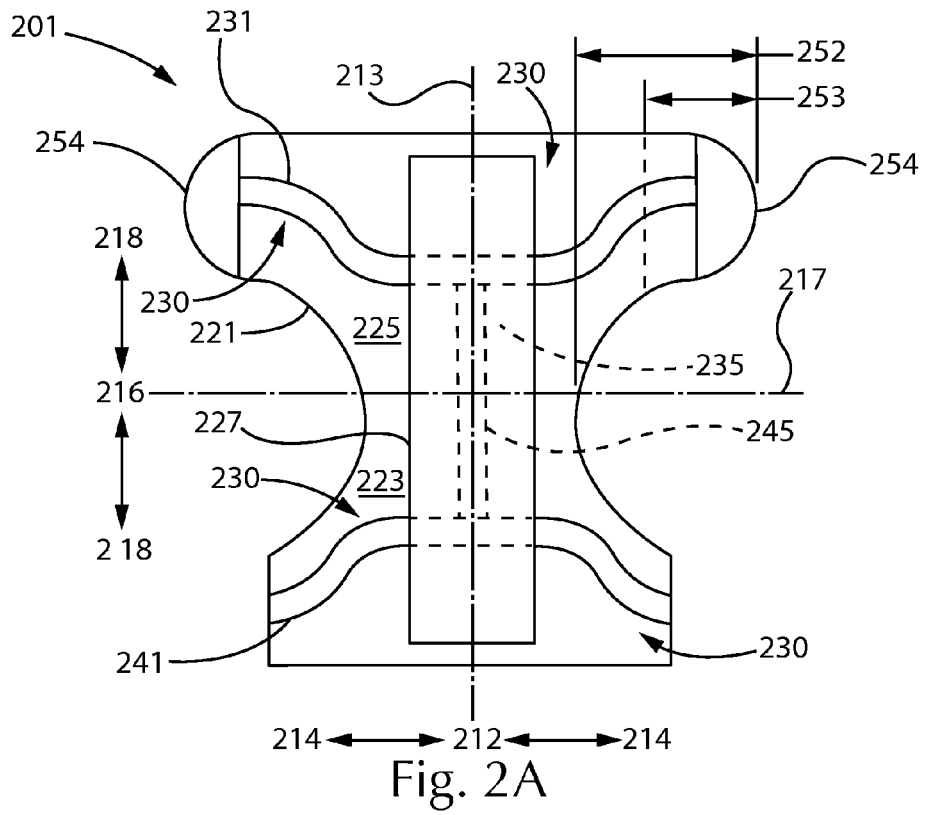
FIG. 2A illustrates a plan view of an inside of a front fastenable wearable absorbent article, which includes an anchoring system.

FIG. 2A illustrates a plan view of an inside of a front fastenable wearable absorbent article 201, which includes an anchoring system 230. The front fastenable wearable absorbent article 201 can be configured as a reusable wearable absorbent article or as a disposable wearable absorbent article. Each of the elements of the embodiment of FIG. 2A is configured in the same way as the like-numbered element of the embodiment of FIG. 1A, except as described below. Throughout the present disclosure, the term "like-numbered" is intended to indicate a correspondence between labels of elements wherein the last two numbers in the labels of the elements are the same. Element labels are considered to be like-numbered despite differing numeral prefixes corresponding to figure numbers, and despite differing suffixes corresponding to particular embodiments.

The first back CAM 231 is joined to one fastener 254 and extends laterally from that one fastener 254, laterally and longitudinally inward through a first portion of the back 225, laterally across, below, and joined to a back portion of the absorbent core 227, laterally and longitudinally outward through a second portion of the back 225, and laterally to the other fastener 254, joining to that other fastener 254. The first back CAM 231 can be configured within the wearable absorbent article 201 in any manner described herein, including any of the alternative embodiments. The first front CAM 241 begins in one side, extends laterally from one longitudinal side edge of the chassis 201, laterally and longitudinally inward through a first portion of the front 223, laterally across, below, and joined to a front portion of the absorbent core 227, laterally and longitudinally outward through a second portion of the front 223, and ends in another side at another longitudinal side edge of the chassis 201. The first front CAM 241 can be configured within the wearable absorbent article 201 in any manner described herein, including any of the alternative embodiments. In various embodiments, the anchoring 230 system could include one or more LDEs in the front 223 or the back 225.

Additionally, any of the embodiments of the front 223 of the wearable absorbent article 201 could be combined with any of the embodiments of a back of any of the front fastenable wearable absorbent articles, as disclosed herein. Further, any of the embodiments of the back 225 of the wearable absorbent article 201 could be combined with any of the embodiments of a front of any of the front fastenable wearable absorbent articles, as disclosed herein, to create further alternate embodiments.

Figure 2B:
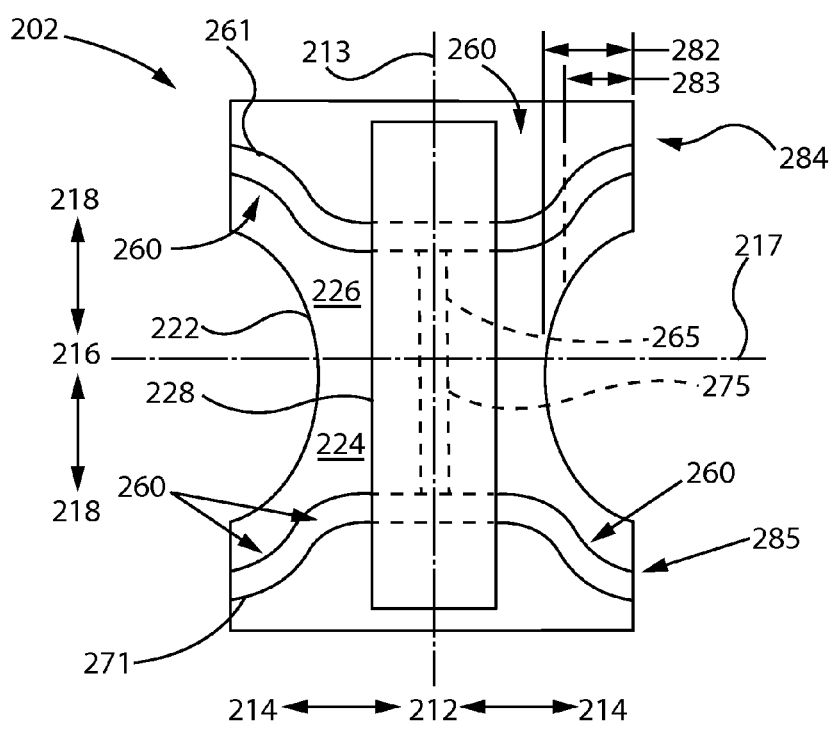
FIG. 2B illustrates a plan view of an inside of a pant type wearable absorbent article, which includes an anchoring system.

FIG. 2B illustrates a plan view of an inside of a pant type wearable absorbent article 202, which includes an anchoring system 260. The pant type wearable absorbent article 202 can be configured as a reusable wearable absorbent article or as a disposable wearable absorbent article. The wearable absorbent article 202 is configured in the same way as the wearable absorbent article 102 of the embodiment of FIG. 1B, except as described below.

The anchoring system 260 is configured in the same way as the anchoring system 230 of the embodiment of FIG. 2A, except for the differences between a pant type wearable absorbent article and a front fastenable wearable absorbent article, as described below. The first back CAM 261 is configured in the same way as the first back CAM 231 of the embodiment of FIG. 2A, except that the first back CAM 261 begins at one longitudinal side edge in a portion of side panel and ends at another longitudinal side edge in another portion of a side panel. The first front CAM 271 is configured in the same way as the first front CAM 241 of the embodiment of FIG. 2A, except that the first front CAM 271 begins at one longitudinal side edge in a portion of side panel and ends at another longitudinal side edge in another portion of a side panel.

Additionally, any of the embodiments of the front 224 of the wearable absorbent article 202 could be combined with any of the embodiments of a back of any of the pant type wearable absorbent articles, as disclosed herein. Further, any of the embodiments of the back 226 of the wearable absorbent article 202 could be combined with any of the embodiments of a front of any of the pant type wearable absorbent articles, as disclosed herein, to create further alternate embodiments.

Figure 3A:
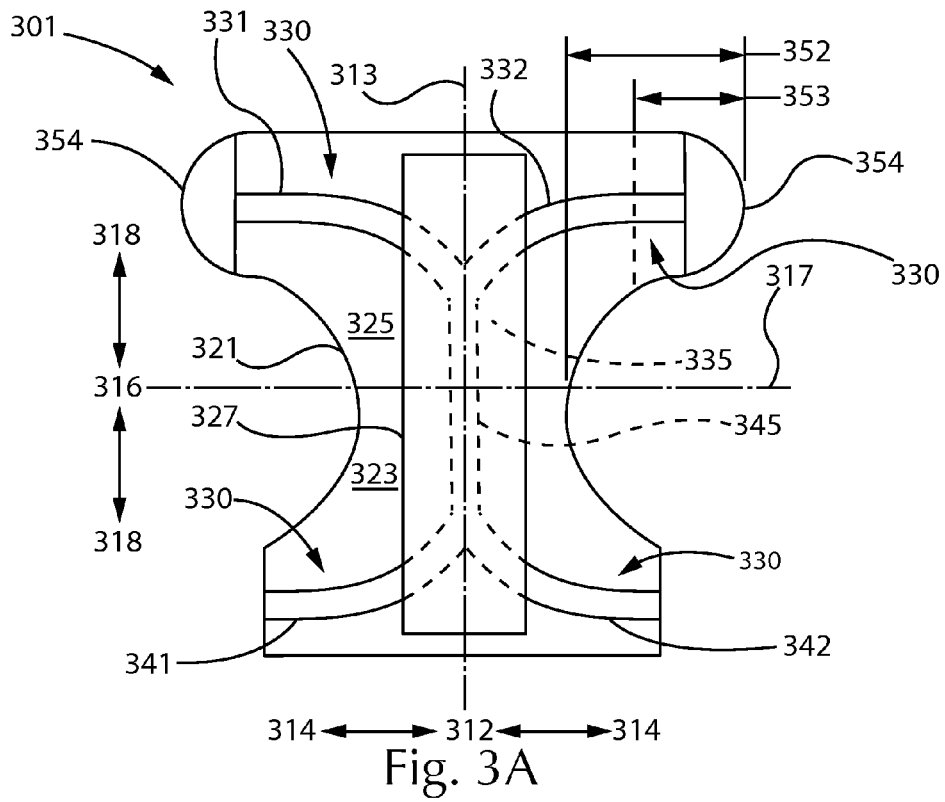
FIG. 3A illustrates a plan view of an inside of a front fastenable wearable absorbent article, which includes an anchoring system.

FIG. 3A illustrates a plan view of an inside of a front fastenable wearable absorbent article 301, which includes an anchoring system 330. The front fastenable wearable absorbent article 301 can be configured as a reusable wearable absorbent article or as a disposable wearable absorbent article. Each of the elements of the embodiment of FIG. 3A is configured in the same way as the like-numbered element of the embodiment of FIG. 1A, except as described below.

The anchoring system 330 includes a first back anchoring band 331 disposed in the back 325, a second back anchoring band 332 disposed in the back, a first front anchoring band 341 disposed in the front 323, a second front anchoring band 342 disposed in the front 323, and a spine 335, 345.

The first back anchoring band 331 is disposed longitudinally inboard to and offset from the longitudinally outboard back edge of the chassis 321. The first back anchoring band 331 is joined to one fastener 354 and extends laterally from that one fastener 354, laterally and longitudinally inward through a first portion of the back 325, laterally and longitudinally inward, below, and joined to a back portion of the absorbent core 327, terminating at an end proximate to the longitudinal centerline 313 and within the area of the back portion of the absorbent core 327. At that end, the first back anchoring band 331 connects to the second back anchoring band 332 and connects to a back portion of the spine 335. The first back anchoring band 331 can be configured within the wearable absorbent article 301 in any manner described herein.

In a first alternate embodiment, part, or parts, or substantially all, or all of the first back anchoring band 331 could be disposed proximate to the longitudinally outboard back end of the absorbent core 327. In a second alternate embodiment, part, or parts, or substantially all, or all of the first back anchoring band 331 could be disposed longitudinally outboard from the longitudinally outboard back end of the absorbent core 327. In a third alternate embodiment, part, or parts, or substantially all, or all of the first back anchoring band 331 could be disposed proximate to the longitudinally outboard back edge of the chassis 321. In a fourth alternate embodiment, part or parts of the first back anchoring band 331 could follow one or more alternate pathways in the side 352 or the side ear 353. In a fifth alternate embodiment, part or parts of the first back anchoring band 331 could connect to one or more additional anchoring elements, as described herein. In a sixth alternate embodiment, the first back anchoring band 331 may not join the fastener 354. In a seventh alternate embodiment, part, or parts, or substantially all, or all of the first back anchoring band 331 may extend through or above the absorbent core 327. In an eighth alternate embodiment, part, or parts, or substantially all, or all of the first back anchoring band 331 may not be joined to the absorbent core 327. In a ninth alternate embodiment, the first back anchoring band 331 could terminate at an end offset from the longitudinal centerline 313 and/or outside of the area of the back portion of the absorbent core 327. In any of these alternate embodiments, part, or parts, or substantially all, or all of the first back anchoring band 331 could be omitted. Also, in any of these alternate embodiments, one or more anchoring bands could be used along part, or parts, or substantially all, or all of the pathway of the first back anchoring band 331. Further, any of these alternate embodiments could be combined in whole or in part to create additional alternate embodiments.

The second back anchoring band 332 can be configured in the same way as the first back anchoring band 331, though mirrored by the longitudinal centerline 313. The second back anchoring band 332 can be configured within the wearable absorbent article 301 in any manner described herein, including any of the alternative embodiments.

The first front anchoring band 341 is disposed longitudinally inboard to and offset from the longitudinally outboard front edge of the chassis 321. The first front anchoring band 341 begins in one side, extends laterally from one longitudinal side edge of the chassis 321, laterally and longitudinally inward through a first portion of the front 325, laterally and longitudinally inward, below, and joined to a front portion of the absorbent core 327, terminating at an end proximate to the longitudinal centerline 313 and within the area of the front portion of the absorbent core 327. At that end, the first front anchoring band 341 connects to the second front anchoring band 342 and connects to a front portion of the spine 335. The first front anchoring band 341 can be configured within the wearable absorbent article 301 in any manner described herein.

In a first alternate embodiment, part, or parts, or substantially all, or all of the first front anchoring band 341 could be disposed proximate to the longitudinally outboard front end of the absorbent core 327. In a second alternate embodiment, part, or parts, or substantially all, or all of the first front anchoring band 341 could be disposed longitudinally outboard from the longitudinally outboard front end of the absorbent core 327. In a third alternate embodiment, part, or parts, or substantially all, or all of the first front anchoring band 341 could be disposed proximate to the longitudinally outboard front edge of the chassis 321. In a fourth alternate embodiment, part or parts of the first front anchoring band 341 could follow one or more alternate pathways in the side 352 or the side ear 353, as described in connection with FIG. 14B. In a fifth alternate embodiment, part or parts of the first front anchoring band 341 could connect to one or more additional anchoring elements, as described herein. In a sixth alternate embodiment, part, or parts, or substantially all, or all of the first front anchoring band 341 may extend through or above the absorbent core 327. In a seventh alternate embodiment, part, or parts, or substantially all, or all of the first front anchoring band 341 may not be joined to the absorbent core 327. In an eighth alternate embodiment, the first front anchoring band 341 could terminate at an end offset from the longitudinal centerline 313 and/or outside of the area of the front portion of the absorbent core 327. In any of these alternate embodiments, part, or parts, or substantially all, or all of the first front anchoring band 341 could be omitted. Also, in any of these alternate embodiments, one or more anchoring bands could be used along part, or parts, or substantially all, or all of the pathway of the first front anchoring band 331. Further, any of these alternate embodiments could be combined in whole or in part to create additional alternate embodiments.

The second front anchoring band 342 can be configured in the same way as the first front anchoring band 341, though mirrored by the longitudinal centerline 313. The second front anchoring band 342 can be configured within the wearable absorbent article 301 in any manner described herein, including any of the alternative embodiments.

When the wearable absorbent article 301 is worn by a wearer, the first front anchoring band 331 and the first back anchoring band 341, together, can be considered a CAM that at least partially encircles the wearer. Similarly, when the wearable absorbent article 301 is worn by a wearer, the second front anchoring band 332 and the second back anchoring band 342, together, can be considered a CAM that at least partially encircles the wearer. Further, when the wearable absorbent article 301 is worn by a wearer, the first front anchoring band 331, the first back anchoring band 341, the second front anchoring band 332, and the second back anchoring band 342, all together, can be considered a single CAM that completely encircles the wearer. In various embodiments, the anchoring 330 system could include one or more LDEs in the front 323 or the back 325.

The back portion of the spine 335 connects to the end of the first back anchoring band 331 and to the end of the second back anchoring band 332. The back portion of the spine 335 is below and joined to a back portion of the absorbent core 327. The back portion of the spine 335 also connects to the front portion of the spine 345. The front portion of the spine 345 connects to the back portion of the spine 335. The front portion of the spine 345 also connects to the end of the first front anchoring band 341 and to the end of the second front anchoring band 342. The front portion of the spine 345 is below and joined to a front portion of the absorbent core 327. The spine 335, 345 is laterally centered on the wearable absorbent article 301. The spine 335, 345 can be configured within the wearable absorbent article 301 in any manner described herein, including any of the alternative embodiments.

Additionally, any of the embodiments of the front 323 of the wearable absorbent article 301 could be combined with any of the embodiments of a back of any of the front fastenable wearable absorbent articles, as disclosed herein. Further, any of the embodiments of the back 325 of the wearable absorbent article 301 could be combined with any of the embodiments of a front of any of the front fastenable wearable absorbent articles, as disclosed herein, to create further alternate embodiments.

Figure 3B:
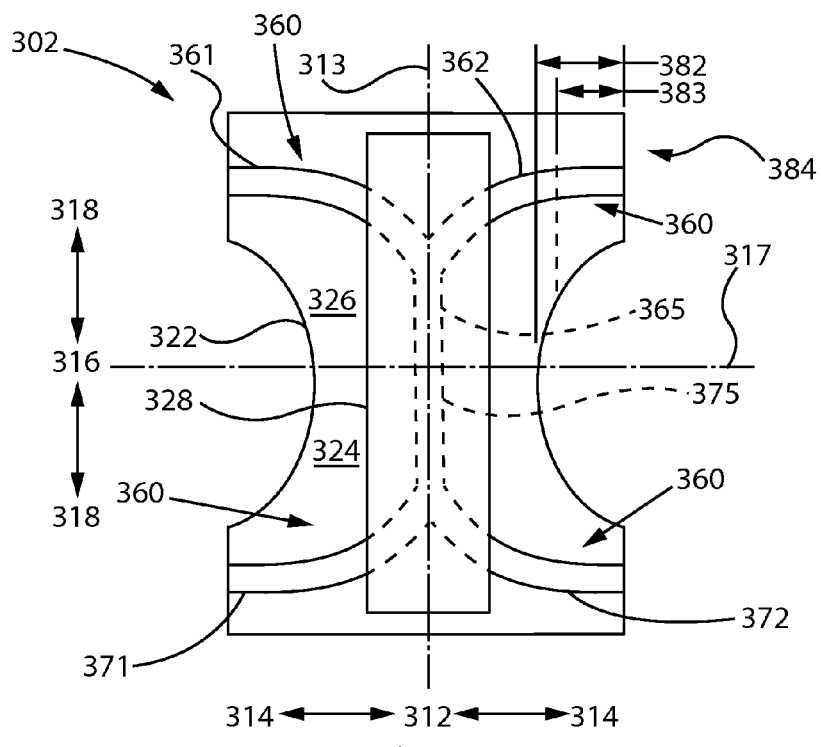
FIG. 3B illustrates a plan view of an inside of a pant type wearable absorbent article, which includes an anchoring system.

FIG. 3B illustrates a plan view of an inside of a pant type wearable absorbent article 302, which includes an anchoring system 360. The pant type wearable absorbent article 302 can be configured as a reusable wearable absorbent article or as a disposable wearable absorbent article. The wearable absorbent article 302 is configured in the same way as the wearable absorbent article 102 of the embodiment of FIG. 1B, except as described below.

The anchoring system 360 is configured in the same way as the anchoring system 330 of the embodiment of FIG. 3A, except for the differences between a pant type wearable absorbent article and a front fastenable wearable absorbent article, as described below. The first back CAM 361 is configured in the same way as the first back CAM 331 of the embodiment of FIG. 3A, except that the first back CAM 361 begins at one longitudinal side edge in a portion of a side panel and ends at another longitudinal side edge in another portion of a side panel. The first front CAM 371 is configured in the same way as the first front CAM 341 of the embodiment of FIG. 3A, except that the first front CAM 371 begins at one longitudinal side edge in a portion of a side panel and ends at another longitudinal side edge in another portion of a side panel.

Additionally, any of the embodiments of the front 324 of the wearable absorbent article 302 could be combined with any of the embodiments of a back of any of the pant type wearable absorbent articles, as disclosed herein. Further, any of the embodiments of the back 326 of the wearable absorbent article 302 could be combined with any of the embodiments of a front of any of the pant type wearable absorbent articles, as disclosed herein, to create further alternate embodiments.

Figure 4A:
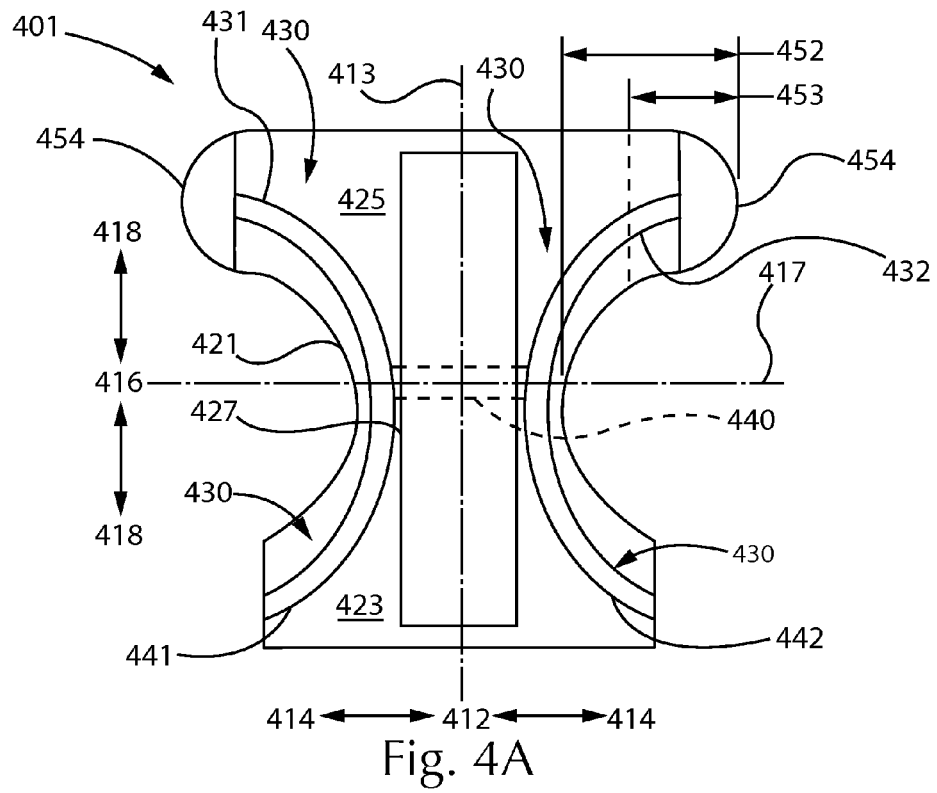
FIG. 4A illustrates a plan view of an inside of a front fastenable wearable absorbent article, which includes an anchoring system.

FIG. 4A illustrates a plan view of an inside of a front fastenable wearable absorbent article 401, which includes an anchoring system 430. The front fastenable wearable absorbent article 401 can be configured as a reusable wearable absorbent article or as a disposable wearable absorbent article. Each of the elements of the embodiment of FIG. 4A is configured in the same way as the like-numbered element of the embodiment of FIG. 1A, except as described below.

The anchoring system 430 includes a first back anchoring band 431 disposed in the back 425, a second back anchoring band 432 disposed in the back, a first front anchoring band 441 disposed in the front 423, a second front anchoring band 442 disposed in the front 423, and a spine 440.

The first back anchoring band 431 is disposed longitudinally inboard to and offset from the longitudinally outboard back edge of the chassis 421. The first back anchoring band 431 is joined to one fastener 454 and extends laterally from that one fastener 454, laterally and longitudinally inward through a first portion of the back 425, longitudinally inward through a second portion of the back 425, terminating at an end proximate to the lateral centerline 417 and outside of the area of the back portion of the absorbent core 427. At that end, the first back anchoring band 431 connects to the first front anchoring band 441 and connects to spine 440. The first back anchoring band 431 is not directly connected to the absorbent core 427. The first back anchoring band 431 can be configured within the wearable absorbent article 401 in any manner described herein.

In a first alternate embodiment, part, or parts, or substantially all, or all of the first back anchoring band 431 could be disposed proximate to the longitudinally outboard back edge of the chassis 421. In a second alternate embodiment, part or parts of the first back anchoring band 431 could follow one or more alternate pathways in the side 452 or the side ear 453. In a third alternate embodiment, part or parts of the first back anchoring band 431 could connect to one or more additional anchoring elements, as described herein. In a fourth alternate embodiment, the first back anchoring band 431 may not join the fastener 454. In a fifth alternate embodiment, part, or parts, or substantially all, or all of the first back anchoring band 431 could be joined to the absorbent core 427. In a sixth alternate embodiment, the first back anchoring band 431 could terminate at an end offset from the lateral centerline 417 and/or within the area of the back portion of the absorbent core 427. In any of these alternate embodiments, part, or parts, or substantially all, or all of the first back anchoring band 431 could be omitted. Also, in any of these alternate embodiments, one or more anchoring bands could be used along part, or parts, or substantially all, or all of the pathway of the first back anchoring band 431. Further, any of these alternate embodiments could be combined in whole or in part to create additional alternate embodiments.

The second back anchoring band 432 can be configured in the same way as the first back anchoring band 431, though mirrored by the longitudinal centerline 413. The second back anchoring band 432 can be configured within the wearable absorbent article 401 in any manner described herein, including any of the alternative embodiments.

The first front anchoring band 441 is disposed longitudinally inboard to and offset from the longitudinally outboard front edge of the chassis 421. The first front anchoring band 441 begins in one side, extends laterally from one longitudinal side edge of the chassis 421, laterally and longitudinally inward through a first portion of the front 425, longitudinally inward through a second portion of the front 425, terminating at an end proximate to the lateral centerline 417 and outside of the area of the front portion of the absorbent core 427. At that end, the first front anchoring band 441 connects to the first back anchoring band 431 and connects to the spine 440. The first front anchoring band 441 is not directly connected to the absorbent core 427. The first front anchoring band 441 can be configured within the wearable absorbent article 401 in any manner described herein.

In a first alternate embodiment, part, or parts, or substantially all, or all of the first front anchoring band 441 could be disposed proximate to the longitudinally outboard front edge of the chassis 421. In a second alternate embodiment, part or parts of the first front anchoring band 441 could follow one or more alternate pathways proximate to either or both of the longitudinal sides, similar to the embodiments described in connection with FIG. 4B. In a third alternate embodiment, part or parts of the first front anchoring band 441 could connect to one or more additional anchoring elements, as described herein. In a fourth alternate embodiment, part, or parts, or substantially all, or all of the first front anchoring band 441 could be joined to the absorbent core 427. In a fifth alternate embodiment, the first front anchoring band 441 could terminate at an end offset from the lateral centerline 417 and/or within the area of the front portion of the absorbent core 427. In any of these alternate embodiments, part, or parts, or substantially all, or all of the first front anchoring band 441 could be omitted. Also, in any of these alternate embodiments, one or more anchoring bands could be used along part, or parts, or substantially all, or all of the pathway of the first front anchoring band 441. Further, any of these alternate embodiments could be combined in whole or in part to create additional alternate embodiments.

The second front anchoring band 442 can be configured in the same way as the first front anchoring band 441, though mirrored by the longitudinal centerline 413. The second front anchoring band 442 can be configured within the wearable absorbent article 401 in any manner described herein, including any of the alternative embodiments.

When the wearable absorbent article 401 is worn by a wearer, the first front anchoring band 431 and the first back anchoring band 441, together, can be considered a CAM that at least partially encircles the wearer. Similarly, when the wearable absorbent article 401 is worn by a wearer, the second front anchoring band 432 and the second back anchoring band 442, together, can be considered a CAM that at least partially encircles the wearer. In various embodiments, the anchoring 430 system could include one or more LDEs in the front 423 or the back 425.

On one side of the longitudinal centerline 413, one end of the spine 440 extends laterally outward from one longitudinal side of the absorbent core 427 to connect with an end of the first back anchoring band 431 and to an end of the first front anchoring band 441. The spine 440 is below and joined to a back portion of the absorbent core 427. On another side of the longitudinal centerline 413, another end of the spine 440 extends laterally outward from another longitudinal side of the absorbent core 427 to connect with an end of the second back anchoring band 432 and to an end of the second front anchoring band 442. The spine 440 is longitudinally centered on the wearable absorbent article 401. The spine 440 can be configured within the wearable absorbent article 401 in any manner described herein.

In a first alternate embodiment, part, or parts, or substantially all, or all of the spine 440 could be disposed offset from the lateral centerline 417, either toward the front 423 or toward the back 425. In a second alternate embodiment, either or both ends of the spine 440 could be disposed within the area of the absorbent core 427. In a third alternate embodiment, the spine 440 could connect to first back anchoring band 431, the second back anchoring band 432, the first front anchoring band 441, and/or the second back anchoring band 442 at one or more additional and/or alternate locations. In a fourth alternate embodiment, part or parts of the spine 440 could connect to one or more additional anchoring elements, as described herein. In a fifth alternate embodiment, the wearable absorbent article 101 could include two or more spines. In a sixth alternate embodiment, part, or parts, or substantially all, or all of the spine 440 may not be joined to the absorbent core 427. In any of these alternate embodiments, part, or parts, or substantially all, or all of the spine 440 could be omitted. In any of these alternate embodiments, one or more anchoring bands could be used along part, or parts, or substantially all, or all of the pathway of the spine 440. Further, any of these alternate embodiments could be combined in whole or in part to create additional alternate embodiments.

Additionally, any of the embodiments of the front 423 of the wearable absorbent article 401 could be combined with any of the embodiments of a back of any of the front fastenable wearable absorbent articles, as disclosed herein. Further, any of the embodiments of the back 425 of the wearable absorbent article 401 could be combined with any of the embodiments of a front of any of the front fastenable wearable absorbent articles, as disclosed herein, to create further alternate embodiments.

Figure 4B:
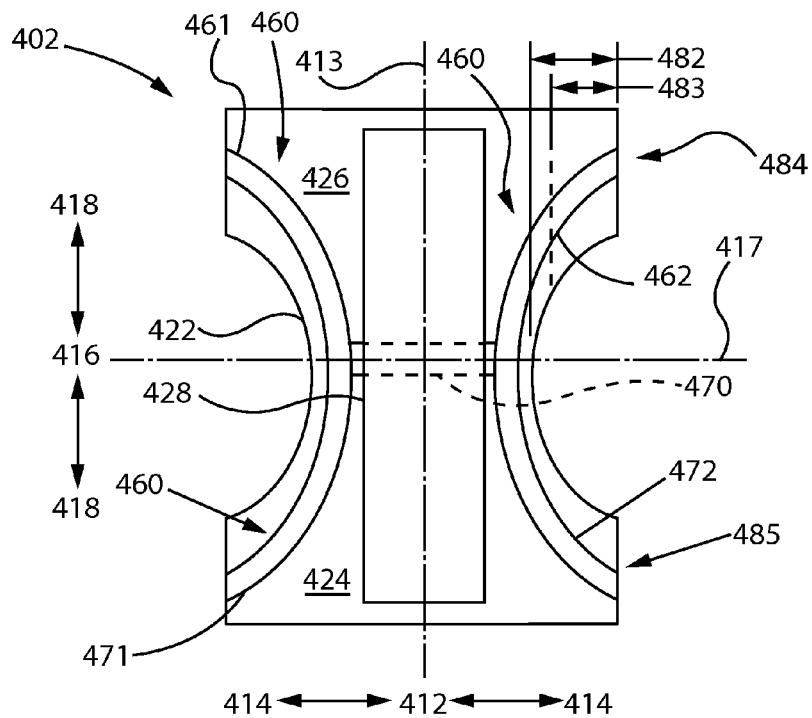
FIG. 4B illustrates a plan view of an inside of a pant type wearable absorbent article, which includes an anchoring system.

FIG. 4B illustrates a plan view of an inside of a pant type wearable absorbent article 402, which includes an anchoring system 460. The pant type wearable absorbent article 402 can be configured as a reusable wearable absorbent article or as a disposable wearable absorbent article. The wearable absorbent article 402 is configured in the same way as the wearable absorbent article 102 of the embodiment of FIG. 1B, except as described below.

The anchoring system 460 is configured in the same way as the anchoring system 430 of the embodiment of FIG. 4A, except for the differences between a pant type wearable absorbent article and a front fastenable wearable absorbent article, as described below. The first back anchoring band 461 is configured in the same way as the first back anchoring band 431 of the embodiment of FIG. 4A, except that the first back anchoring band 461 begins at one longitudinal side edge in a portion of a side panel and ends at another longitudinal side edge in another portion of a side panel. The second back anchoring band 462 is configured in the same way as the first back anchoring band 461, though mirrored by the longitudinal centerline 413. The first front anchoring band 471 is configured in the same way as the first front anchoring band 441 of the embodiment of FIG. 4A, except that the first front anchoring band 471 begins at one longitudinal side edge in a portion of a side panel and ends at another longitudinal side edge in another portion of a side panel. The second front anchoring band 472 is configured in the same way as the first front anchoring band 471, though mirrored by the longitudinal centerline 413.

Additionally, any of the embodiments of the front 424 of the wearable absorbent article 402 could be combined with any of the embodiments of a back of any of the pant type wearable absorbent articles, as disclosed herein. Further, any of the embodiments of the back 426 of the wearable absorbent article 402 could be combined with any of the embodiments of a front of any of the pant type wearable absorbent articles, as disclosed herein, to create further alternate embodiments.

Figure 5A:
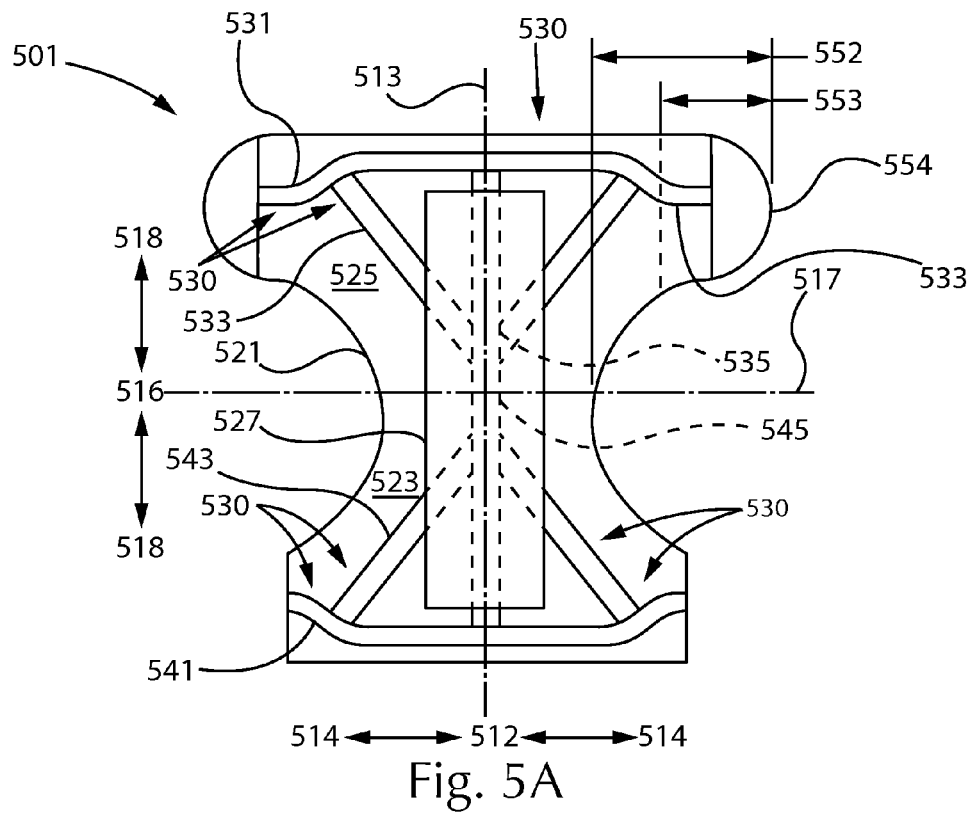
FIG. 5A illustrates a plan view of an inside of a front fastenable wearable absorbent article, which includes an anchoring system.

FIG. 5A illustrates a plan view of an inside of a front fastenable wearable absorbent article 501, which includes an anchoring system 530. The front fastenable wearable absorbent article 501 can be configured as a reusable wearable absorbent article or as a disposable wearable absorbent article. Each of the elements of the embodiment of FIG. 5A is configured in the same way as the like-numbered element of the embodiment of FIG. 1A, except as described below.

The first back CAM 531 is joined to one fastener 554 and extends laterally from that one fastener 554, laterally inward and longitudinally outward through a first portion of the back 525, laterally across, longitudinally outboard from a longitudinally outboard back edge of the absorbent core 527, laterally outward and longitudinally inward through a second portion of the back 525, and laterally to the other fastener 554, joining to that other fastener 554. The first back CAM 531 is not directly connected to the absorbent core 527. The first back CAM 531 can be configured within the wearable absorbent article 501 in any manner described herein, including any of the alternative embodiments. The back LDEs 533 are configured in the same way as the back LDEs 133 of the embodiment of FIG. 1A, except that the back LDEs 533 connect with the first back CAM 531 at locations further longitudinally outboard.

The first front CAM 541 begins in one side, extends laterally from one longitudinal side edge of the chassis 501, laterally inward and longitudinally outward through a first portion of the front 523, laterally across, longitudinally outboard from a longitudinally outboard front edge of the absorbent core 527, laterally outward and longitudinally inward through a second portion of the front 523, and ends in another side at another longitudinal side edge of the chassis 501. The first front CAM 541 is not directly connected to the absorbent core 527. The first front CAM 541 can be configured within the wearable absorbent article 501 in any manner described herein, including any of the alternative embodiments. The front LDEs 543 are configured in the same way as the front LDEs 143 of the embodiment of FIG. 1A, except that the front LDEs 543 connect with the first back CAM 531 at locations further longitudinally outboard.

The spine 535, 545 is configured in the same way as the spine 135, 145 of the embodiment of FIG. 1A, except as described below. The back portion of the spine 535 extends longitudinally outward from the longitudinally outboard back edge of the absorbent core 527 to connect with the first back CAM 531. The front portion of the spine 545 extends longitudinally outward from the longitudinally outboard front edge of the absorbent core 527 to connect with the first back CAM 541. The spine 535, 545 can be configured within the wearable absorbent article 501 in any manner described herein, including any of the alternative embodiments.

Additionally, any of the embodiments of the front 523 of the wearable absorbent article 501 could be combined with any of the embodiments of a back of any of the front fastenable wearable absorbent articles, as disclosed herein. Further, any of the embodiments of the back 525 of the wearable absorbent article 501 could be combined with any of the embodiments of a front of any of the front fastenable wearable absorbent articles, as disclosed herein, to create further alternate embodiments.

Figure 5B:
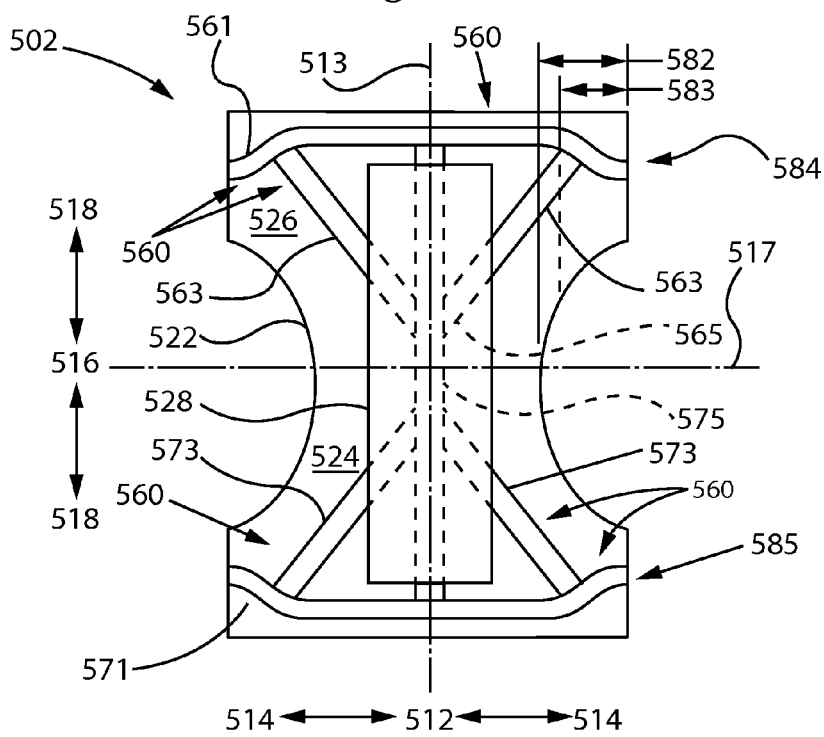
FIG. 5B illustrates a plan view of an inside of a pant type wearable absorbent article, which includes an anchoring system.

FIG. 5B illustrates a plan view of an inside of a pant type wearable absorbent article 502, which includes an anchoring system 560. The pant type wearable absorbent article 502 can be configured as a reusable wearable absorbent article or as a disposable wearable absorbent article. The wearable absorbent article 502 is configured in the same way as the wearable absorbent article 102 of the embodiment of FIG. 1B, except as described below.

The anchoring system 560 is configured in the same way as the anchoring system 530 of the embodiment of FIG. 5A, except for the differences between a pant type wearable absorbent article and a front fastenable wearable absorbent article, as described below. The first back CAM 561 is configured in the same way as the first back CAM 531 of the embodiment of FIG. 5A, except that the first back CAM 561 begins at one longitudinal side edge in a portion of side panel and ends at another longitudinal side edge in another portion of a side panel. The first front CAM 571 is configured in the same way as the first front CAM 541 of the embodiment of FIG. 5A, except that the first front CAM 571 begins at one longitudinal side edge in a portion of side panel and ends at another longitudinal side edge in another portion of a side panel.

Additionally, any of the embodiments of the front 524 of the wearable absorbent article 502 could be combined with any of the embodiments of a back of any of the pant type wearable absorbent articles, as disclosed herein. Further, any of the embodiments of the back 526 of the wearable absorbent article 502 could be combined with any of the embodiments of a front of any of the pant type wearable absorbent articles, as disclosed herein, to create further alternate embodiments.

In various alternate embodiments, a front fastenable wearable absorbent article can include combinations of part, or parts, or substantially all, or all of one or more of any of the anchoring systems disclosed herein for front fastenable wearable absorbent articles. As some examples, a front fastenable wearable absorbent article could include the anchoring system 130 of FIG. 1A combined with: (1) the anchoring system 230 of FIG. 2A; (2) the anchoring system 330 of FIG. 3A; (3) the anchoring system 430 of FIG. 4A; or (4) the anchoring system 530 of FIG. 5A; either in the front, or the back, or the front and the back. As some other examples, a front fastenable wearable absorbent article could include the anchoring system 530 of FIG. 5A combined with: (1) the anchoring system 230 of FIG. 2A; (2) the anchoring system 330 of FIG. 3A; or (3) the anchoring system 430 of FIG. 4A; either in the front, or the back, or the front and the back. Such combinations can be made with any of the alternate embodiments disclosed herein.

In such alternate embodiments, wherein a front fastenable wearable absorbent article includes combinations of one or more anchoring systems, anchoring elements can follow one or more alternate pathways in either or both sides, in the front and/or in the back of the article. In one exemplary alternate embodiment of a front fastenable wearable absorbent article, the pathways of anchoring elements may connect together into a single pathway. In another exemplary alternate embodiment of a front fastenable wearable absorbent article, the pathways of anchoring elements may connect together into a single pathway and then split apart into a plurality of pathways. In yet another exemplary alternate embodiment of a front fastenable wearable absorbent article, the pathways of anchoring elements may not connect together, but may continue as separate pathways.

Also, in various alternate embodiments, a pant type wearable absorbent article can include combinations of part, or parts, or substantially all, or all of one or more of any of the anchoring systems disclosed herein for pant type wearable absorbent articles. As some examples, a pant type wearable absorbent article could include the anchoring system 160 of FIG. 1B combined with: (1) the anchoring system 260 of FIG. 2B; (2) the anchoring system 360 of FIG. 3B; (3) the anchoring system 460 of FIG. 4B; or (4) the anchoring system 560 of FIG. 5B; either in the front, or the back, or the front and the back. As some other examples, a pant type wearable absorbent article could include the anchoring system 560 of FIG. 5B combined with: (1) the anchoring system 260 of FIG. 2B; (2) the anchoring system 360 of FIG. 3B; or (3) the anchoring system 460 of FIG. 4B; either in the front, or the back, or the front and the back. Such combinations can be made with any of the alternate embodiments disclosed herein.

Also, in such alternate embodiments, wherein a pant type wearable absorbent article includes combinations of one or more anchoring systems, anchoring elements can follow one or more alternate pathways in either or both sides, in the front and/or in the back of the article. In one exemplary alternate embodiment of a pant type wearable absorbent article, the pathways of anchoring elements may connect together into a single pathway. In another exemplary alternate embodiment of a pant type wearable absorbent article, the pathways of anchoring elements may connect together into a single pathway and then split apart into a plurality of pathways. In yet another exemplary alternate embodiment of a pant type wearable absorbent article, the pathways of anchoring elements may not connect together, but may continue as separate pathways.

Embodiments of the present disclosure include wearable absorbent articles with anchoring systems that fit wearers well. The designs of these articles help prevent the articles from sagging or slipping down on a wearer. As a result, the wearable absorbent articles of the present disclosure can feel comfortable, look attractive, and perform well as the articles tend to stay in place on wearers and not leak.

To determine whether a component of an absorbent article, such as an outer cover, is launderable or laundering resistant, the component is machine washed and machine dried according to the protocol from AATCC (American Association of Textile Chemists and Colorists) Test Method 124-2001, with the selected parameters and substitutions listed below.

AATCC Test Method 124-2001 a) Per section 6, Apparatus and materials, a Kenmore 600 (Heavy Duty—Super Capacity Plus—Quiet Pak) is used for the automatic washing machine, and a Maytag Commercial (such as model numbers MDE27MNACW, MDE15MNAYW, and MDE13MNACW) is used for the automatic tumble dryer.

b) Despite the instructions in Section 6, Apparatus and materials, the following ballast is used: Test Fabric style 493 from Testfabrics, Inc, West Pittston, Pa., which is cotton sheeting, with a thread count of 60×60, a weight of 151 gsm, and a size of 55' by 39".

c) Despite the instructions in Section 6, Apparatus and materials, the evaluation area is not configured according to section 6.7 and the apparatus of section 6.8 is not used. Instead, all visual evaluations are performed under typical artificial lighting conditions (e.g. fluorescent light), which allows a person with normal vision to clearly see.

d) Despite the instructions in Section 7, Test Specimen, the component to be tested is (as necessary) entirely removed from the rest of the absorbent article, and (to the extent allowed by the removal) the component is tested as an undamaged whole. Up to three components of the same type are washed simultaneously.

e) Regarding the machine wash in Section 8.2.2, use the "large" setting on the machine for the water level, select a wash temperature of 32+/−3° C. (90+/−5° F.), and a rinse temperature of 16+/−3° C. (60+/−5° F.).

f) Regarding the settings in Section 8.2.2, select Normal/Cotton Sturdy, which has a washing time of 12 minutes, an initial spin time of 6 minutes, a refill time of 4 minutes, a rinse time of 5 minutes, and a final spin cycle time of 6 minutes.

g) Regarding the Drying in Section 8.3, select Cotton Sturdy and Whites & Colors.

h) Despite the instructions in Section 8.5, the steps of conditioning and preconditioning are not performed.

i) Despite the instructions in Section 9, Evaluation, these evaluation steps are not performed. Instead, the tested component is evaluated by one of skill in the art, to determine whether the testing has resulted in significant degradation to the appearance or performance of the article that would render it unsuitable for its intended functionality and/or use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable absorbent article comprising:
a reusable outer cover; and
a disposable absorbent core comprising barrier leg cuffs and fasteners for retaining the absorbent core to the reusable outer cover;
the reusable outer cover configured to form an outside of the wearable absorbent article, the reusable outer cover comprising a lateral axis defining a front and a back, and an anchoring system configured to anchor the absorbent core to a wearer of the article, wherein the anchoring system comprises:
a first load distribution element in the back;
a second load distribution element in the back;
a third load distribution element in the front;
a fourth load distribution element in the front;
a first circumferential anchoring member in the back;
a second circumferential anchoring member in the front; and
a spine extending from the first circumferential anchoring member to the second circumferential anchoring member along a longitudinal axis of the reusable outer cover, wherein the first and second load distribution elements engage the spine and the first circumferential anchoring member in the back, wherein the third and fourth load distribution elements engage the spine and the second circumferential anchoring member in the front, and wherein the circumferential anchoring members, the load distribution elements, and the spine are all individual elements.

2. The wearable absorbent article of claim 1, wherein the reusable outer cover comprises a waist edge forming a waist opening when the article is worn, and wherein the anchoring system is spaced apart from the waist edge.

3. The wearable absorbent article of claim 2, wherein the reusable outer cover comprises a waist band disposed proximate to the waist edge.

4. The wearable absorbent article of claim 3, wherein at least a portion of the anchoring system is joined to the reusable outer cover.

5. The wearable absorbent article of claim 1, wherein the reusable outer cover comprises a first side ear and a second side ear, and wherein one end of the first circumferential anchoring member is joined to the first side ear and another end of the first circumferential anchoring member is joined to the second side ear.

6. The wearable absorbent article of claim 5, wherein the first circumferential anchoring member is not prestretched with respect to the reusable outer cover.

7. The wearable absorbent article of claim 5, wherein the reusable outer cover comprises an inner layer and an outer layer, and wherein the first circumferential anchoring member is disposed between the inner layer and the outer layer.

8. The wearable absorbent article of claim 7, wherein the first circumferential anchoring member is laterally elastically extensible.

9. The wearable absorbent article of claim 8, wherein the reusable outer cover has a first lateral modulus of elasticity, and wherein the first circumferential anchoring member has a second lateral modulus of elasticity that is greater than the first lateral modulus of elasticity.

10. The wearable outer cover of claim 1, wherein the disposable absorbent core comprises a wetness indicator.

11. The wearable outer cover of claim 1, wherein the disposable absorbent core comprises a feces containment compartment.

12. The wearable outer cover of claim 1, wherein the disposable absorbent core comprises a disposal tape.

* * * * *